United States Patent
Ozaki

(10) Patent No.: US 9,573,947 B2
(45) Date of Patent: *Feb. 21, 2017

(54) SALT OF PYRAZOLOQUINOLINE DERIVATIVE, AND CRYSTAL THEREOF

(71) Applicant: Eisai R&D Management Co., Ltd., Bunkyo-ku, Tokyo (JP)

(72) Inventor: Shunsuke Ozaki, Kamisu (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/778,695

(22) PCT Filed: Apr. 3, 2014

(86) PCT No.: PCT/JP2014/059853
§ 371 (c)(1),
(2) Date: Sep. 21, 2015

(87) PCT Pub. No.: WO2014/163147
PCT Pub. Date: Oct. 9, 2014

(65) Prior Publication Data
US 2016/0046623 A1    Feb. 18, 2016

(30) Foreign Application Priority Data
Apr. 5, 2013    (JP) ................. 2013-079639

(51) Int. Cl.
| C07D 471/04 | (2006.01) |
| A61K 31/4745 | (2006.01) |
| C07C 57/145 | (2006.01) |
| C07C 309/29 | (2006.01) |

(52) U.S. Cl.
CPC ......... *C07D 471/04* (2013.01); *A61K 31/4745* (2013.01); *C07C 57/145* (2013.01); *C07C 309/29* (2013.01); *C07B 2200/13* (2013.01)

(58) Field of Classification Search
CPC ............... C07D 471/04; A61K 31/4745
USPC ............................... 546/82; 514/290
See application file for complete search history.

(56) References Cited

U.S. PATENT DOCUMENTS

| 8,563,565 B2 * | 10/2013 | Norimine ............ C07D 471/04 514/213.01 |
| 2006/0035920 A1 | 2/2006 | Boyle et al. |
| 2009/0131467 A1 | 5/2009 | Kanazawa et al. |
| 2010/0048556 A1 | 2/2010 | Okada et al. |
| 2011/0082137 A1 | 4/2011 | Giovannini et al. |
| 2011/0184000 A1 | 7/2011 | Giovannini et al. |
| 2011/0319385 A1 | 12/2011 | Kaizawa et al. |
| 2013/0085134 A1 | 4/2013 | Kaizawa et al. |
| 2013/0143907 A1 | 6/2013 | Norimine et al. |
| 2013/0225553 A1 | 8/2013 | Kaizawa et al. |
| 2013/0225572 A1 | 8/2013 | Okada et al. |

FOREIGN PATENT DOCUMENTS

| CA | 2754457 | 9/2010 |
| CN | 101553491 | 10/2009 |
| CN | 101983199 | 3/2011 |
| EP | 1925617 | 5/2008 |
| EP | 2103613 | 9/2009 |
| JP | H5-132484 | 5/1993 |
| JP | H9-506634 | 6/1997 |
| JP | 2006-045118 | 2/2006 |
| JP | 2011-516454 | 5/2011 |
| JP | 2013-067595 | 4/2013 |
| JP | WO 2013051639 A1 * | 4/2013 ........... C07D 471/04 |
| JP | 5546693 | 5/2014 |
| RU | 2426734 | 8/2011 |
| WO | WO 95/32205 | 11/1995 |
| WO | WO 2007/032466 | 3/2007 |
| WO | WO 2008/072779 | 6/2008 |
| WO | WO 2008/139293 | 11/2008 |
| WO | WO 2009/121919 | 10/2009 |
| WO | WO 2010/101230 | 9/2010 |
| WO | WO 2012/033144 | 3/2012 |
| WO | WO 2013/045400 | 4/2013 |
| WO | WO 2013/051639 | 4/2013 |

OTHER PUBLICATIONS

Response to Office Action in Chilean Application No. 2014-00821, dated Aug. 19, 2015, 26 pages, with English translation.
Office Action in Chilean Application No. 2014-00821, dated Oct. 29, 2015, 11 pages, with English translation.
Office Action in Israeli Application No. 241695, dated Jan. 24, 2016, 5 pages, with English translation.
Bonkale et al., "Reduced Nitric Oxide Responsive Soluble Guanylyl Cyclase Activity in the Superior Temporal Cortex of Patients with Alzheimer's Disease," Neurosci Lett, 1995, 187:5-8.
Brandon and Rotella, "Potential CNS 8 Applications for Phosphodiesterase Enzyme Inhibitors," Annual Reports in Medicinal Chemistry, Dec. 2007, 42:3-12.
Chinese Observations in Chinese Application No. 201480016592.4, dated Nov. 4, 2015, 2 pages, with English translation.
Chinese Office Action in Chinese Application No. 201280046653.2, dated Feb. 28, 2015, 10 pages, with English translation.
Chinese Office Action in Chinese Application No. 201480016592.4, dated Oct. 16, 2015, 2 pages, with English translation.
Columbian Office Action in Columbian Application No. 14-059034, dated Mar. 10, 2015, 13 pages, with English translation.
Domek-Lopacinska and Strosznajder, "Cyclic GMP Metabolism and its Role in Brain Physiology," J Phys and Pharma, 2005, 56(S2):15-34.
Extended European Search Report in European Application No. 12837953.4, dated Jan. 27, 2015, 10 pages.

(Continued)

*Primary Examiner* — Rita Desai
(74) *Attorney, Agent, or Firm* — Fish & Richardson P.C.

(57) ABSTRACT

The present invention provides a salt of (S)-7-(2-methoxy-3,5-dimethylpyridin-4-yl)-1-(tetrahydrofuran-3-yl)-1H-pyrazolo[4,3-c]quinolin-4(5H)-one and an acid selected from the group consisting of hydrochloric acid, hydrobromic acid, sulfuric acid, nitric acid, phosphoric acid, malonic acid, maleic acid, tartaric acid, methanesulfonic acid, benzenesulfonic acid and toluenesulfonic acid; or a crystal thereof with a potential to be used as drug substance in pharmaceuticals.

11 Claims, 13 Drawing Sheets

(56) References Cited

OTHER PUBLICATIONS

Fisher et al., "Isolation and Characterization of PDE9A, a Novel Human cGMP-specific Phosphodiesterase," J Biol Chem, 1998, 273(25):15559-15564.
International Preliminary Report on Patentability in International Application No. PCT/JP2012/075748, dated Apr. 17, 2014, 10 pages.
International Preliminary Report on Patentability in International Application No. PCT/JP2014/059852, dated Oct. 15, 2015, 8 pages.
International Preliminary Report on Patentability in International Application No. PCT/JP2014/059853, dated Oct. 15, 2015, 7 pages.
International Search Report in International Application No. PCT/JP2012/075748, dated Nov. 20, 2012, 2 pages.
Israeli Office Action in Israeli Application No. 231650, dated Jul. 16, 2014, 4 pages, with English translation.
Japanese Notice of Allowance in Japanese Application No. P2013-537544, dated Apr. 30, 2014, 6 pages, with English translation.
Japanese Office Action in Japanese Application No. P2014-538559, dated Sep. 30, 2014, 4 pages, with English translation.
New Zealand Office Action in New Zealand Application No. 622594, dated Feb. 4, 2015, 2 pages.
Pakistani Office Action in Pakistani Application No. 672/2012, dated Feb. 14, 2013, 8 pages.
Response to Chinese Office Action dated Feb. 28, 2015 in Chinese Application No. 201280046653.2, dated Apr. 28, 2015, 16 pages, with English translation.
Response to Columbian Office Action dated Mar. 10, 2015 in Columbian Application No. 14-059034, dated Jul. 16, 2015, 23 pages, with English translation.
Response to Extended European Search Report dated Jan. 27, 2015 in European Application No. 12837953.4, dated May 15, 2015, 22 pages.
Response to Israeli Office Action Dated Jul. 16, 2014 in Israeli Application No. 231650, dated Nov. 6, 2014, 8 pages, with English translation.
Response to New Zealand Office Action dated Feb. 4, 2015 in New Zealand Application No. 622594, dated May 22, 2015, 16 pages.
Response to Vietnamese Office Action dated Nov. 25, 2015 in Vietnamese Application No. 1-2015-03459, dated Dec. 17, 2015, 21 pages, with English translation.
South American Notice of Allowance in South American Application No. 2014/02439, dated Jan. 21, 2015, 3 pages.
Takano et al., "Oral Absorption of Poorly Water-Soluble Drugs: Computer Simulation of Fraction Absorbed in Humans From a Miniscale Dissolution Test," Pharm Res, Jun. 2006, 23(6):1144-1156.
United States Notice of Allowance in U.S. Appl. No. 13/644,745, dated Jun. 10, 2013, 13 pages.
United States Office Action in U.S. Appl. No. 13/644,745, dated Mar. 26, 2013, 8 pages.
Van der Staay et al., "The Novel Selective PDE9 Inhibitor BAY 73-6691 Improves Learning and Memory in Rodents," Neurophannacology, 2008, 55(5):908-918.
Vietnamese Office Action in Vietnamese Application No. 1-2015-03459, dated Nov. 25, 2015, 2 pages, with English translation.
Wang and Robinson, "Cyclic GMP-Dependent Protein Kinase and Cellular Signaling in the Nervous System," J Neurochem, 1997, 68(2):443-459.
Response to Office Action in Chilean Application No. 2014-00821, dated Dec. 16, 2015, 6 pages, with English translation.
Office Action in Israeli Application No. 241796, dated Jan. 24, 2016, 5 pages, with English translation.
Request to Amend Application Before Grant in Singapore Application No. 11201400717Q, dated Feb. 12, 2016, 9 pages.
Chinese Submission Documents in Application No. 2014/80017423.2, dated Jul. 4, 2016, 6 pages, with English translation.
Filipino Submission Documents in Application No. 1-2014-500580, dated Aug. 30, 2016, 3 pages.
GCC Submission Documents in Application No. GC2012-22447, dated Jul. 18, 2016, 4 pages, with English tmnslation.
Malaysian Submission Documents in Application No. PI2014700702, dated Sep. 28, 2016, 12 pages, with English translation.
Pakistani Submission Documents in Application No. 672/2012, dated Jul. 28, 2016, 17 pages, with English tmnslation.
Russian Notice of Allowance in Application No. 2014112931, dated Aug. 22, 2016, 19 pages, with English translation.
Taiwanese Notice of Allowance in Application No. 101136747, dated Aug. 17, 2016, 5 pages, with English translation.
Taiwanese Submission Documents in Application No. 101136747, dated Jul. 21, 2016, 15 pages, with English translation.
Australian Notice of Allowance in Application No. 2012319549, dated Jul. 19, 2016, 3 pages.
Australian Office Action in Application No. 2012319549, dated Jun. 1, 2016, 7 pages.
Australian Response to Examination Report in Application No. 2012319549, dated Jul. 8, 2016, 6 pages.
Chinese Office Action in Application No. 201480016592.4, dated May 12, 2016, 12 pages, with English translation.
Chinese Office Action in Application No. 201480017423.2, dated Mar. 1, 2016, 10 pages, with English translation.
Chinese Submission Documents in Application No. 2014/0017423.2, dated Jul. 4, 2016, 6 pages, with English translation.
European Response to Office Action in Application No. 14780073.4, dated May 11, 2016, 5 pages.
European Response to Office Action in Application No. 14780139.3, dated May 10, 2016, 4 pages.
European Search Report in Application No. 14780073.4, dated Jul. 28, 2016, 4 pages.
European Search Report in Application No. 14780139.3, Jul. 13, 2016, 5 pages.
Filipino Office Action in Application No. 1-2014-500580, dated Jun. 17, 2016, 3 pages.
Filipino Submission Documents in Application No. 1-2014-500580, dated Jul. 21, 2016, 5 pages.
GCC Office Action in Application No. GC2012-22447, dated Apr. 21, 2016, 4 pages.
Israeli Notice of Allowance in Application No. 231650, dated Feb. 10, 2016, 5 pages, with English translation.
Israeli Response to Office Action in Application No. 241695, dated May 23, 2016, 4 pages.
Israeli Response to Office Action in Application No. 241796, dated May 23, 2016, 4 pages, with English translation.
Russian Response to Office Action in Application No. 2014112931, dated Jul. 26, 2016, 23 pages, with English translation.
Singapore Notice of Allowance in Application No. 11201400717Q, dated May 26, 2016, 4 pages.
Taiwanese Office Action in Application No. 101136747, dated Apr. 22, 2016, 5 pages, with English translation.
Thai Submission Documents in Application No. 1401001864, dated Feb. 15, 2016, 352 pages, with English translation.

* cited by examiner

SEQUENCE LISTING

<160> NUMBER OF SEQ ID NOS: 2

<210> SEQ ID NO 1
<211> LENGTH: 22
<212> TYPE: DNA
<213> ORGANISM: Artificial
<220> FEATURE:
<223> OTHER INFORMATION: hPDE9-1

<400> SEQUENCE: 1
aggatgggat ccggctcctc ca                     22

<210> SEQ ID NO 2
<211> LENGTH: 21
<212> TYPE: DNA
<213> ORGANISM: Artificial
<220> FEATURE:
<223> OTHER INFORMATION: hPDE9A-3

<400> SEQUENCE: 2
caggcacagt ctccttcact g                      21

SALT OF PYRAZOLOQUINOLINE DERIVATIVE, AND CRYSTAL THEREOF

TECHNICAL FIELD

The present invention relates to salts of pyrazoloquinoline derivatives having inhibitory activity against phosphodiesterase 9 (PDE9), and crystal thereof.

BACKGROUND ART

Cyclic guanosine monophosphate (hereinafter, referred to as cGMP) functioning as a second messenger in cells is known to play an important role in various physiological functions including learning and memory behaviors.

On the postsynaptic site of the brain neural circuits, nitrogen monoxide (hereinafter, referred to as NO) biosynthesized by a nitrogen monoxide synthetase activates a guanylate cyclase, which is a cGMP synthetase. The activated guanylate cyclase biosynthesizes cGMP from guanosine triphosphate. The cGMP activates a cGMP-dependent protein kinase (hereinafter, referred to as PKG) to phosphorylate various proteins participating in synapse plasticity. The activation of the NO/cGMP/PKG cascade is known to participate in the induction of synapse plasticity (Long Term Potentiation; hereinafter, referred to as LTP) of the hippocampus known as a neural substrate for learning and memory behaviors (for example, see Non Patent Literature 1). A medicine activating the signal transmission of the cascade is known to improve LTP of the hippocampus and the learning behavior of animals, while a medicine inhibiting the cascade is known to exhibit the opposite action (Non Patent Literature 2). Therefore, from these findings, an increase in cGMP in the brain is anticipated to lead to an improvement of learning and memory behaviors.

cGMP is metabolized to 5'-GMP having no PKG activation action by a phosphodiesterase (hereinafter, referred to as PDE). The PDE is known to have 11 families, and PDE9 is known to metabolize specifically cGMP, and to be expressed in the brain, the spleen, the small intestine and the like (for example, see Non Patent Literature 3). That is, inhibition of PDE9 is anticipated to increase cGMP in brains. It is reported that a PDE9 inhibitor actually enhances hippocampus LTP, and improves the learning and memory behaviors in a novel-object recognition test/passive avoidance learning test or the like in animals (Non Patent Literature 4). Clinically, guanylate cyclase activity decreases and possibility of a decrease in the cGMP level is indicated in the superior temporal cortex of Alzheimer's disease patients, (Non Patent Literature 5). Therefore, the PDE9 has a possibility of having many close relations with pathologies of neurodegenerative diseases and psychiatric diseases, particularly with pathologies of cognitive dysfunctions and the like in the Alzheimer's disease, such as Alexander's disease, Alpers' disease, Alzheimer's disease, amyotrophic lateral sclerosis (ALS; known as Lou Gehrig's disease or motor neuron disease), ataxia-telangiectasia, Batten's disease (known also as Spielmeyer-Vogt-Sjogren-Batten's disease), Binswanger's dementia (subcortical angiosclerotic encephalopathy), bipolar disorder, bovine spongiform encephalopathy (BSE), Canavan's disease, chemotherapy induction dementia, Cockayne's syndrome, corticobasal degeneration, Creutzfeldt-Jakob's disease, depression, Down's syndrome, frontotemporal lobe degeneration (including frontotemporal dementia, semantic dementia and progressive nonfluent aphasia), Gerstmann-Straussler-Scheinker's disease, glaucoma, Huntington's disease (chorea), HIV related dementia, hyperkinesis, Kennedy's disease, Korsakoffs syndrome (amnesic confabulation syndrome), Krabbe's disease, Lewy-bodies dementia, progressive logopenic aphasia, Machado-Joseph's disease (spinocerebellar ataxia type 3), multiple sclerosis, multiple atrophy (olivopontocerebellar atrophy), myasthenia gravis, Parkinson's disease, Pelizaeus-Merzbacher's disease, Pick's disease, dementia presenilis (slight cognitive impairment), primary lateral sclerosis, primary progressive aphasia, radiation-induced dementia, Refsum's disease (phytanic acid storage disease), Sandhoffs disease, Schilder's disease, schizophrenia, semantic dementia, senile dementia, Shy-Drager syndrome, spinocerebellar ataxia, spinal muscle atrophy, Steele-Richardson-Olszewski's disease (progressive supranuclear palsy), and vascular amyloidosis and vascular dementia (multiple infarct dementia).

CITATION LIST

Non Patent Literature

[Non Patent Literature 1] Domek-Lopacinska et al., "Cyclic GMP metabolism and its role in brain physiology", J Physiol Pharmacol., vol. 56, Suppl 2: pp. 15-34, 2005

[Non Patent Literature 2] Wang X., "Cyclic GMP-dependent protein kinase and cellular signaling in the nervous system", J. Neurochem., vol. 68, pp. 443-456, 1997

[Non Patent Literature 3] Fisher et al., "Isolation and characterization of PDE9A, a novel human cGMP-specific phosphodiesterase", J. Biol. Chem., vol. 273: pp. 15559-15564, 1998

[Non Patent Literature 4] van der Stony et al., "The novel selective PDE9 inhibitor BAY 73-6691 improves learning and memory in rodents", Neuropharmacology, vol. 55: pp. 908-918, 2008

[Non Patent Literature 5] Bonkale et al., "Reduced nitric oxide responsive soluble guanylyl cyclase activity in the superior temporal cortex of patients with Alzheimer's disease", Neurosci. Left., vol 187, pp. 5-8, 1995

SUMMARY OF INVENTION

Technical Problem

A compound represented by the following formula (I) ((S)-7-(2-methoxy-3,5-dimethylpyridin-4-yl)-1-(tetrahydrofuran-3-yl)-1H-pyrazolo[4,3-c]quinolin-4(5H)-one; hereafter referred to as compound (I)) was found as a novel compound with PDE9 inhibitory activity, and a patent application for those inventions was filed (PCT/JP2012/075748):

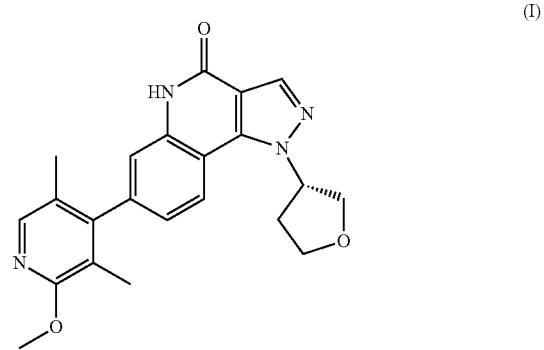 [SMILES: COc1ncc(C)c(-c2ccc3c(c2)[nH]c(=O)c2cnn([C@H]4CCOC4)c23)c1C]

(I)

Concerning compounds with a potential to be used as pharmaceuticals, the physical properties of salts thereof or crystals of the salts generally have huge effects on the bioavailability of the drug, purity of the drug substances, pharmaceutical formulations and the like.

An object of the present invention is therefore to provide a salt of compound (I) or a crystal thereof with a potential to be used as drug substance in pharmaceuticals, and with improved dissolution and oral absorption characteristics.

Solution to Problem

The present inventors have extensively examined compound (I) to solve the above-described problems, and as a result, have found salts of compound (I) or crystals thereof, thereby completing the invention.

Thus, the present invention relates to:

[1] a salt of (S)-7-(2-methoxy-3,5-dimethylpyridin-4-yl)-1-(tetrahydrofuran-3-yl)-1H-pyrazolo[4,3-c]quinolin-4(5H)-one and an acid selected from the group consisting of hydrochloric acid, hydrobromic acid, sulfuric acid, nitric acid, phosphoric acid, malonic acid, maleic acid, tartaric acid, methanesulfonic acid, benzenesulfonic acid and toluenesulfonic acid;

[2] (S)-7-(2-methoxy-3,5-dimethylpyridin-4-yl)-1-(tetrahydrofuran-3-yl)-1H-pyrazolo[4,3-c]quinolin-4(5H)-one monomaleate salt;

[3] (S)-7-(2-methoxy-3,5-dimethylpyridin-4-yl)-1-(tetrahydrofuran-3-yl)-1H-pyrazolo[4,3-c]quinolin-4(5H)-one monobenzenesulfonate salt;

[4] a crystal of the salt according to [1];

[5] a crystal of (S)-7-(2-methoxy-3,5-dimethylpyridin-4-yl)-1-(tetrahydrofuran-3-yl)-1H-pyrazolo[4,3-c]quinolin-4(5H)-one monomaleate salt, having a diffraction peak at a diffraction angle ($2\theta \pm 0.2°$) of 10.1° in powder X-ray diffraction;

[6] a crystal of (S)-7-(2-methoxy-3,5-dimethylpyridin-4-yl)-1-(tetrahydrofuran-3-yl)-1H-pyrazolo[4,3-c]quinolin-4(5H)-one monobenzenesulfonate salt, having a diffraction peak at a diffraction angle ($2\theta \pm 0.2°$) of 9.9° in powder X-ray diffraction;

[7] a pharmaceutical composition comprising the salt according to [1] as an active ingredient;

[P1] a salt of (S)-7-(2-methoxy-3,5-dimethylpyridine-4-yl)-1-(tetrahydrofuran-3-yl)-1H-pyrazolo[4,3-c]quinoline-4(5H)-one and an acid selected from the group consisting of inorganic acids, organic carboxylic acids and organic sulfonic acids;

[P2] the salt according to [P1], wherein the acid is an organic carboxylic acid;

[P3] the salt according to [P2], wherein the organic carboxylic acid is malonic acid, maleic acid or tartaric acid;

[P4] the salt according to [P1], wherein the acid is an organic sulfonic acid;

[P5] the salt according to [P4], wherein the organic sulfonic acid is methanesulfonic acid, benzenesulfonic acid or toluenesulfonic acid;

[P6] the salt according to [P1], wherein the acid is an inorganic acid;

[P7] the salt according to [P6], wherein the inorganic acid is hydrochloric acid, hydrobromic acid, sulfuric acid, nitric acid or phosphoric acid;

[P8] (S)-7-(2-methoxy-3,5-dimethylpyridin-4-yl)-1-(tetrahydrofuran-3-yl)-1H-pyrazolo[4,3-c]quinolin-4(5H)-one monomaleate salt;

[P9] (S)-7-(2-methoxy-3,5-dimethylpyridin-4-yl)-1-(tetrahydrofuran-3-yl)-1H-pyrazolo[4,3-c]quinolin-4(5H)-one monobenzenesulfonate salt;

[P10] a crystal of the salt according to [P1];

[P11] the crystal according to [P10], wherein the acid is malonic acid, maleic acid, tartaric acid, methanesulfonic acid, benzenesulfonic acid, toluenesulfonic acid, hydrochloric acid, hydrobromic acid, sulfuric acid, nitric acid or phosphoric acid;

[P12] a crystal of (S)-7-(2-methoxy-3,5-dimethylpyridin-4-yl)-1-(tetrahydrofuran-3-yl)-1H-pyrazolo[4,3-c]quinolin-4(5H)-one monomaleate salt, having a diffraction peak at a diffraction angle ($2\theta \pm 0.2°$) of 10.1° in powder X-ray diffraction;

[P12.1] a crystal of (S)-7-(2-methoxy-3,5-dimethylpyridin-4-yl)-1-(tetrahydrofuran-3-yl)-1H-pyrazolo[4,3-c]quinolin-4(5H)-one monomaleate salt, having diffraction peaks at diffraction angles ($2\theta \pm 0.2°$) of 9.1° and 10.1° in powder X-ray diffraction;

[P12.2] a crystal of (S)-7-(2-methoxy-3,5-dimethylpyridin-4-yl)-1-(tetrahydrofuran-3-yl)-1H-pyrazolo[4,3-c]quinolin-4(5H)-one monomaleate salt, having diffraction peaks at diffraction angles ($2\theta \pm 0.2°$) of 9.1°, 10.1° and 11.1° in powder X-ray diffraction; [P12.3] a crystal of (S)-7-(2-methoxy-3,5-dimethylpyridin-4-yl)-1-(tetrahydrofuran-3-yl)-1H-pyrazolo[4,3-c]quinolin-4(5H)-one monomaleate salt, having diffraction peaks at diffraction angles ($2\theta \pm 0.2°$) of 9.1°, 10.1°, 11.1°, 18.2° and 25.8° in powder X-ray diffraction;

[P12.4] a crystal of (S)-7-(2-methoxy-3,5-dimethylpyridin-4-yl)-1-(tetrahydrofuran-3-yl)-1H-pyrazolo[4,3-c]quinolin-4(5H)-one monomaleate salt, having diffraction peaks at diffraction angles ($2\theta \pm 0.2°$) of 9.1°, 10.1°, 11.1°, 16.2°, 17.6°, 18.2°, 22.0°, 22.4°, 23.8° and 25.8° in powder X-ray diffraction;

[P12.5] a crystal of (S)-7-(2-methoxy-3,5-dimethylpyridin-4-yl)-1-(tetrahydrofuran-3-yl)-1H-pyrazolo[4,3-c]quinolin-4(5H)-one monomaleate salt, having peaks at chemical shifts (ppm) of 13.3, 61.9, 114.3, 138.9 and 172.0 in a $^{13}C$ solid-state NMR spectrum;

[P13] a crystal of (S)-7-(2-methoxy-3,5-dimethylpyridin-4-yl)-1-(tetrahydrofuran-3-yl)-1H-pyrazolo[4,3-c]quinolin-4(5H)-one monobenzenesulfonate salt, having a diffraction peak at a diffraction angle ($2\theta \pm 0.2°$) of 9.9° in powder X-ray diffraction;

[P13.1] a crystal of (S)-7-(2-methoxy-3,5-dimethylpyridin-4-yl)-1-(tetrahydrofuran-3-yl)-1H-pyrazolo[4,3-c]quinolin-4(5H)-one monobenzenesulfonate salt, having diffraction peaks at diffraction angles ($2\theta \pm 0.2°$) of 9.9° and 14.6° in powder X-ray diffraction;

[P13.2] a crystal of (S)-7-(2-methoxy-3,5-dimethylpyridin-4-yl)-1-(tetrahydrofuran-3-yl)-1H-pyrazolo[4,3-c]quinolin-4(5H)-one monobenzenesulfonate salt, having diffraction peaks at diffraction angles ($2\theta \pm 0.2°$) of 9.9°, 13.7° and 14.6° in powder X-ray diffraction;

[P13.3] a crystal of (S)-7-(2-methoxy-3,5-dimethylpyridin-4-yl)-1-(tetrahydrofuran-3-yl)-1H-pyrazolo[4,3-c]quinolin-4(5H)-one monobenzenesulfonate salt, having diffraction peaks at diffraction angles ($2\theta \pm 0.2°$) of 6.6°, 9.9°, 13.7°, 14.6° and 25.7° in powder X-ray diffraction;

[P13.4] a crystal of (S)-7-(2-methoxy-3,5-dimethylpyridin-4-yl)-1-(tetrahydrofuran-3-yl)-1H-pyrazolo[4,3-c]quinolin-4(5H)-one monobenzenesulfonate salt, having diffraction peaks at diffraction angles ($2\theta \pm 0.2°$) of 6.6°, 9.9°, 13.7°, 14.6°, 19.0°, 19.6°, 20.5°, 21.7°, 23.5° and 25.7° in powder X-ray diffraction;

[P13.5] a crystal of (S)-7-(2-methoxy-3,5-dimethylpyridin-4-yl)-1-(tetrahydrofuran-3-yl)-1H-pyrazolo[4,3-c]quinolin-4(5H)-one monobenzenesulfonate salt, having peaks at chemical shifts (ppm) of 16.8, 67.9, 114.0, 137.7 and 160.7 in a $^{13}$C solid-state NMR spectrum;

[P14] a pharmaceutical composition comprising the salt according to [P1] as an active ingredient;

[P14.1] a pharmaceutical composition comprising the salt according to [P8] or [P9] as an active ingredient;

[P14.2] a pharmaceutical composition comprising the crystal according to [P12], [P12.1], [P12.2], [P12.3], [P12.4] or [P12.5] as an active ingredient; and

[P14.3] a pharmaceutical composition comprising the crystal according to [P13], [P13.1], [P13.2], [P13.3], [P13.4] or [P13.5] as an active ingredient.

Advantageous Effects of Invention

The salts of compound (I) and the crystals thereof provided by the present invention possess improved dissolution and oral absorption characteristics and a potential to be used as drug substance in pharmaceuticals.

DESCRIPTION OF EMBODIMENTS

Figure 1:
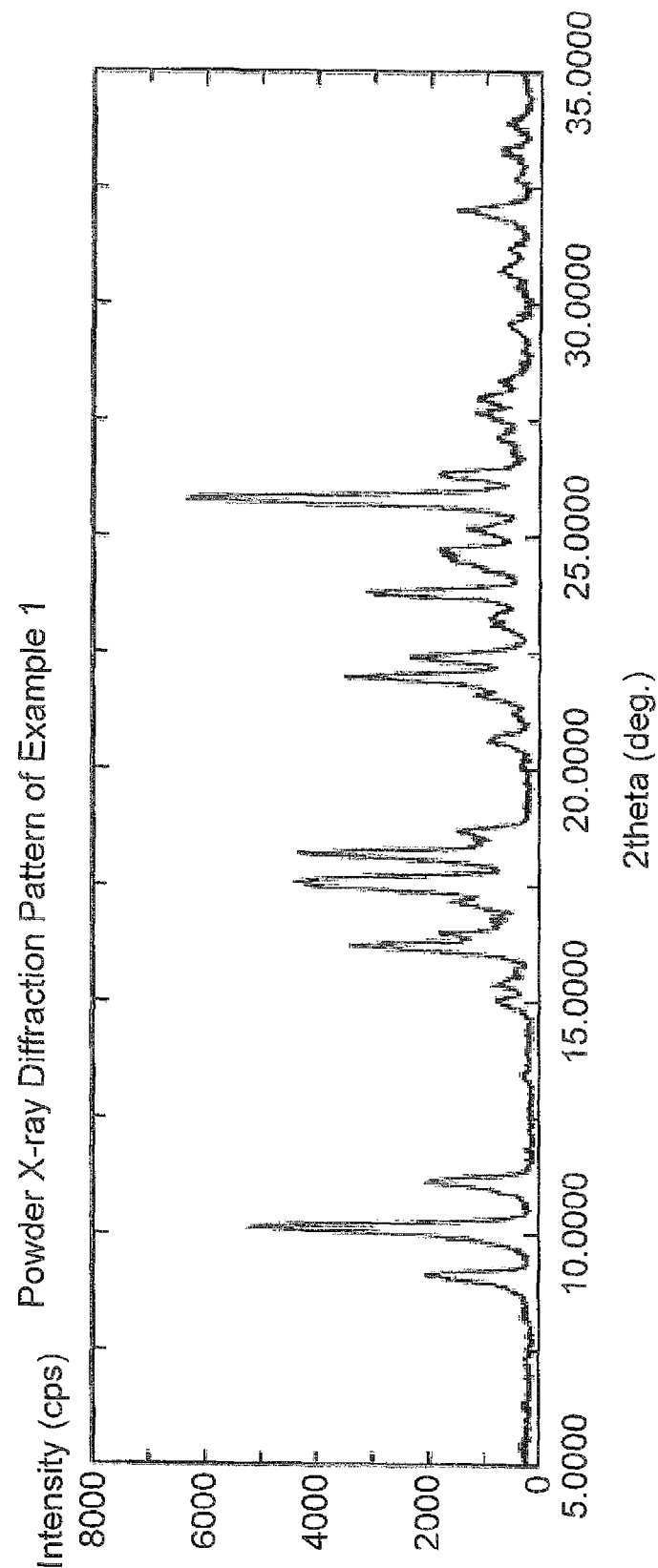
FIG. 1 is a powder X-ray diffraction pattern of the crystal of the compound (I) monomaleate salt obtained in Example 1. The abscissa shows the diffraction angle (2θ) and the ordinate shows the peak intensity.

The salts, the crystals and the methods for producing them according to the present invention will be illustrated in detail below.

As used herein, a "salt" means a "salt in its commonly used meaning" or a cocrystal, containing compound (I) with PDE9 inhibitory activity and a pharmaceutically acceptable acid. The "salt in its commonly used meaning" refers to a compound composed of a positively charged component of basic compound (I) and a negatively charged component of an acid. Furthermore, the cocrystal refers to a crystalline complex in which the molecules of compound (I) and the acid are packed within the crystal lattice in a constant ratio and in a constant configuration.

Specifically, a salt according to the present invention is a salt in its commonly used meaning or a cocrystal containing compound (I) and an acid selected from the group consisting of organic carboxylic acids, organic sulfonic acids and inorganic acids.

Examples of organic carboxylic acids preferably include acetic acid, oxalic acid, maleic acid, tartaric acid, fumaric acid, citric acid and malonic acid salt, and more preferably maleic acid, tartaric acid and malonic acid.

Examples of organic sulfonic acids preferably include methanesulfonic acid, trifluoromethanesulfonic acid, ethanesulfonic acid, benzenesulfonic acid, toluenesulfonic acid and camphorsulfonic acid, and more preferably methanesulfonic acid, benzenesulfonic acid and toluenesulfonic acid.

Examples of inorganic acids preferably include hydrofluoric acid, hydrochloric acid, hydrobromic acid, hydroiodic acid, sulfuric acid, nitric acid, perchloric acid, phosphoric acid, carbonic acid and bicarbonic acid, and more preferably hydrochloric acid, hydrobromic acid, sulfuric acid, nitric acid and phosphoric acid.

Salts according to the present invention may be solvates. As used herein, a "solvate of a salt of compound (I)" refers to a solid that the salt of compound (I) and solvent molecules together form. Examples of solvents in the solvates include ketone solvents such as acetone, 2-butanone and cyclohexanone; ester solvents such as methyl acetate and ethyl acetate; ether solvents such as 1,2-dimethoxyethane and t-butyl methyl ether; alcohol solvents such as methanol, ethanol, 1-propanol and isopropanol, polar solvents such as N-methyl-2-pyrrolidone, N,N-dimethylformamide and dimethylsulfoxide; and water.

As used herein, a "crystal" refers to a crystal of a salt of compound (I). Accordingly, a crystal of compound (I) monomaleate salt, for example, means a crystal of a salt in its commonly used meaning formed between compound (I) and maleic acid, or a cocrystal formed between compound (I) and maleic acid.

Examples of crystals preferred herein include a crystal of a compound (I) monomaleate salt, having a diffraction peak at a diffraction angle (2θ±0.2°) of 10.1° in powder X-ray diffraction;

a crystal of a compound (I) monomaleate salt, having diffraction peaks at diffraction angles (2θ±0.2°) of 9.1° and 10.1° in powder X-ray diffraction;

a crystal of a compound (I) monomaleate salt, having diffraction peaks at diffraction angles (2θ±0.2°) of 9.1°, 10.1° and 11.1° in powder X-ray diffraction;

a crystal of a compound (I) monomaleate salt, having diffraction peaks at diffraction angles (2θ±0.2°) of 9.1°, 10.1°, 11.1°, 18.2° and 25.8° in powder X-ray diffraction;

a crystal of a compound (I) monomaleate salt, having diffraction peaks at diffraction angles (2θ±0.2°) of 9.1°, 10.1°, 11.1°, 16.2°, 17.6°, 18.2°, 22.0°, 22.4°, 23.8° and 25.8° in powder X-ray diffraction;

a crystal of a compound (I) monobenzenesulfonate salt, having a diffraction peak at a diffraction angle (2θ±0.2°) of 9.9° in powder X-ray diffraction;

a crystal of a compound (I) monobenzenesulfonate salt, having diffraction peaks at diffraction angles (2θ±0.2°) of 9.9° and 14.6° in powder X-ray diffraction;

a crystal of a compound (I) monobenzenesulfonate salt, having diffraction peaks at diffraction angles (2θ±0.2°) of 9.9°, 13.7° and 14.6° in powder X-ray diffraction;

a crystal of a compound (I) monobenzenesulfonate salt, having diffraction peaks at diffraction angles (2θ±0.2°) of 6.6°, 9.9°, 13.7°, 14.6° and 25.7° in powder X-ray diffraction;

a crystal of a compound (I) monobenzenesulfonate salt, having diffraction peaks at diffraction angles (2θ±0.2°) of 6.6°, 9.9°, 13.7°, 14.6°, 19.0°, 19.6°, 20.5°, 21.7°, 23.5° and 25.7° in powder X-ray diffraction; or a crystal of a compound (I) monomaleate salt, characterized by having peaks at chemical shifts (ppm) of 13.3, 61.9, 114.3, 138.9 and 172.0 in a $^{13}C$ solid-state NMR spectrum;

a crystal of a compound (I) monobenzenesulfonate salt, characterized by having peaks at chemical shifts (ppm) of 16.8, 67.9, 114.0, 137.7 and 160.7 in a $^{13}C$ solid-state NMR spectrum.

The peaks in powder X-ray diffraction, described above, are characteristic of the respective crystals of the compound (I) monomaleate salts or that of the compound (I) monobenzenesulfonate salts.

Generally, errors in diffraction angles (2θ) within the range of ±0.2° may arise in powder X-ray diffraction, and thus the above-described values of diffraction angles need to be considered to include values within the range of approximately ±0.2°. Included in the present invention are, therefore, not only crystals with peaks at exactly the same diffraction angles in powder X-ray diffraction, but also crystals with peaks within an error range of approximately ±0.2° of the diffraction angles.

Hence, "having a diffraction peak at a diffraction angle (2θ±0.2°) of 10.1°" as used herein, for example, means "having a diffraction peak at a diffraction angle (2θ) of 9.9° to 10.3°". The same is also applied to other diffraction angles.

As used herein, "having peaks at chemical shifts (ppm) of 13.3, 61.9, 114.3, 138.9 and 172.0" means "having peaks each substantially equivalent to the peaks at chemical shifts (ppm) of 13.3, 61.9, 114.3, 138.9 and 172.0, when $^{13}C$ solid-state NMR spectrometry is performed under a conventional measurement condition or substantially the same condition as in the present specification".

When determining whether "having peaks substantially equivalent to" or not, the above-described values of the chemical shifts need to be considered to include values within the range of approximately ±0.5 ppm since generally errors in chemical shifts (ppm) within the range of ±0.5 ppm may arise in a $^{13}C$ solid-state NMR spectrum. Included in the present invention are, therefore, not only crystals with exactly the same chemical shifts in a $^{13}C$ solid-state NMR spectrum, but also crystals with chemical shifts within an error range of approximately ±0.5 ppm. Hence, "having a peak at chemical shift (ppm) of 13.3" as used herein, for example, means "having a peak at a chemical shift (ppm) of 12.8 to 13.8". The same is also applied to other chemical shifts in $^{13}C$ solid-state NMR spectra.

The method for producing salts of compound (I) or crystals or the like thereof, which are one embodiment according to the present invention, will be illustrated below.

Production of Compound (I)

Compound (I) according to the present invention can be synthesized from 3-oxotetrahydrofuran, 2-fluoro-5-methylpyridine and 4-bromo-2-fluorobenzoic acid as the starting materials as described specifically in Reference Example 1 below Methods for Producing Salts of Compound (I)

Salts of compound (I) can be obtained by conventional methods for producing salts. Specifically, they can be produced, for example, by suspending or dissolving compound (I) in a solvent, with heating if necessary, then by adding to the obtained suspension or solution an acid selected from the group consisting of organic carboxylic acids, organic sulfonic acids and inorganic acids, and by stirring or leaving the resultant suspension or solution for several minutes to several days at room temperature or with ice-bath cooling. Salts of compound (I) may be obtained as crystals or amorphous substances according to the production methods. Examples of the solvents to be used in these methods include alcohol solvents such as ethanol, 1-propanol and isopropanol; acetonitrile; ketone solvents such as acetone and 2-butanone; ester solvents such as ethyl acetate; saturated hydrocarbon solvents such as hexane and heptane; ether solvents such as t-butyl methyl ether or water. Each of these solvents may be used alone, or two or more may be mixed and used.

In the above-described methods for producing the compound (I), the salts of compound (I) may be produced subsequent to the synthesis of compound (I) by employing the foregoing methods.

Methods for Producing Crystals of Salts of Compound (I)

A crystal of a salt of compound (I) may be produced by the above-mentioned methods for producing salts of compound (I), or by heat-dissolving the salt of compound (I) in a solvent and crystallizing it through cooling with stirring.

The salt of compound (I) to be used in the crystallization may be in any form: it may be a hydrate, an anhydride, an amorphous substance, a crystalline substance (including those consisting of a plurality of crystalline polymorphs) or a combination thereof.

Examples of the solvents to be used in the crystallization include alcohol solvents such as methanol, ethanol, isopropanol and 1-propanol; acetonitrile; amide solvents such as N,N-dimethylformamide; ester solvents such as ethyl acetate; saturated hydrocarbon solvents such as hexane and heptane; ketone solvents such as acetone and 2-butanone; ether solvents such as t-butyl methyl ether or water. Furthermore, each of these solvents may be used alone, or two or more may be mixed and used.

The amount of the solvent to be used may be suitably selected, provided that the lower limit is the amount with which the free form of compound (I) or the salt thereof is dissolved by heating or the suspension can be stirred, and that the upper limit is the amount with which the yield of the crystal is not significantly reduced.

The crystal obtained by the above-described methods is in a single-crystal form. This crystal form is stable, does not readily convert to other crystal forms or amorphous substances, possesses good physical properties, and is suitable also for formulation.

A seed crystal (e.g., the crystal of the desired salt of compound (I)) may be added or may not be added during the crystallization. The temperature at which the seed crystal is added is not particularly limited, but is preferably 0 to 60° C.

As the temperature to be employed when the salt of compound (I) is dissolved by heating, that at which compound (I) dissolves may be suitably selected depending on the solvent, but it is preferably within the range between the temperature at which the recrystallization solvent starts to reflux and 50° C., and more preferably 65 to 55° C.

Cooling during the crystallization could give substances containing different forms of crystals (polymorphism) in the case of rapid cooling. It is therefore desirable to perform the cooling while controlling the cooling rate as appropriate based on the consideration of its effect on the quality, grain size and the like of the crystal. Preferred is, for example, cooling at a cooling rate of 40 to 5° C./hour. More preferred is cooling at a cooling rate of for example, 25 to 5° C./hour.

Furthermore, the final crystallization temperature may be selected suitably for the yield, quality and the like of the crystal, but is preferably 30 to −25° C.

The target crystal can be obtained by isolating the formed crystal through a conventional filtration procedure, washing the filtered-off crystal with a solvent if necessary, and further drying it. As the solvent to be used for washing the crystal, the same solvent as in the crystallization can be used Preferably, it is, for example, acetone, 2-butanone, ethyl acetate, t-butyl methyl ether and a mixed solvent of hexane/2-butanone (2:3 volume ratio).

The crystal isolated through the filtration procedure may be dried appropriately by leaving it in air or under nitrogen flow, or by heating.

As the drying time, the time until the amount of residual solvent becomes less than the predefined amount may be selected as appropriate depending on the amount of production, the drying apparatus, the drying temperature and the like. Furthermore, drying may be performed under airflow or under reduced pressure. The degree of pressure reduction may be selected as appropriate depending on the amount of production, the drying apparatus, the drying temperature and the like. The obtained crystal may be left in air as required after drying.

In the above-mentioned methods for producing compound (I), the above-described crystals may be produced subsequent to the synthesis of compound (I) by further employing the above-mentioned methods for producing salts of compound (I), and if necessary, the methods for producing crystals of salts of compound (I).

The salts of compound (I) and the crystals thereof obtained by the above-explained production methods are expected to increase the concentration of cGMP in the brain since they possess PDE9 inhibitory activity as shown by the activity data in the exemplary pharmacological test described later. PDE9 inhibitory activity and the increase in cGMP in the brain leads to improvement of learning and memory behavior, and those salts and crystals have a potential to be used as a therapeutic agent for cognitive dysfunction and the like in Alzheimer's disease.

A compound of the formula (I) according to the present invention or a pharmaceutically acceptable salt thereof can be pharmaceutically prepared by a conventional method, and the dosage form can be made, for example, an oral preparation, (tablet, granule, powder, capsule, syrup, or the like), an injection (for intravenous administration, for intramuscular administration, for subcutaneous administration, for intraperitoneal administration, and for others), and an external preparation (endermic preparation (ointment, patch, and the like), eyedrops, nasal drops, suppository, and the like).

In the case of producing an oral solid preparation, to a compound of the formula (I) or a pharmaceutically acceptable salt thereof, as required, an excipient, a binder, a disintegrant, a lubricant, a colorant and the like are added, and a tablet, a granule, a powder and a capsule can be produced by conventional methods. The tablet, granule, powder, capsule and the like, as required, may be film-coated.

Examples of the excipient include lactose, cornstarch and crystalline cellulose; examples of the binder include hydroxypropyl cellulose and hydroxypropyl methyl cellulose; examples of the disintegrant include carboxymethyl cellulose calcium and croscarmellose sodium; examples of the lubricant include magnesium stearate and calcium stearate; examples of the colorant include titanium oxide; and examples of the film coating agent include hydroxypropyl cellulose, hydroxypropyl methyl cellulose and methyl cellulose, but these additives are of course not limited to these examples.

These solid preparations such as tablets, capsules, granules and powders can each contain usually 0.001 to 99.5% by weight, preferably 0.01 to 90% by weight or the like, of a compound of the formula (I) or a pharmaceutically acceptable salt thereof.

In the case of producing an injection (for intravenous administration, for intramuscular administration, for subcutaneous administration, for intraperitoneal administration, and for others), to a compound of the formula (I) or a pharmaceutically acceptable salt thereof, as required, a pH regulator, a buffering agent, a suspending agent, a solubilizer, an antioxidant, a preservative (antiseptic), an isotonic agent, and the like are added, and an injection can be produced by a conventional method. The preparations may be lyophilized to be made extemporaneous dissolution-type lyophilized preparations.

As the pH regulator and the buffering agent, an organic acid or an inorganic acid and/or a salt thereof or the like, for example, can be used. Furthermore, as the suspending agent, methylcellulose, polysorbate 80, carboxymethyl cellulose sodium or the like, for example, can be used. As the solubilizer, polysorbate 80, polyoxyethylene sorbitan monolaurate or the like, for example, can be used. As the antioxidant, α-tocopherol or the like, for example, can be used. As the preservative, methyl parahydroxybenzoate, ethyl parahydroxybenzoate or the like, for example, can be used. As the isotonic agent, glucose, sodium chloride, mannitol or the like, for example, can be used. The pH regulator, the buffering agent, the suspending agent, the solubilizer, the antioxidant, the preservative (antiseptic) and the isotonic agent are of course not limited to these.

These injections can commonly contain 0.000001 to 99.5 mass %, and preferably 0.00001 to 90 mass % or the like of the salt of compound (I) or the crystal thereof, in relation to the total mass of the injections.

In the case of producing an external preparation, a basis raw material is added to a compound of the formula (I) or a pharmaceutically acceptable salt thereof, and as required, for example, the preservative, a stabilizer, the pH regulator, the antioxidant, the colorant and the like are added, and for example, an endermic preparation (ointment, patch, and the like), eyedrops, nasal drops, suppository, and the like can be produced by conventional methods.

As basis raw materials to be used, various raw materials usually used, for example, for medicines, quasi-drugs and cosmetics can be used. Specific examples thereof include raw materials such as animal and vegetable oils, mineral oils, ester oils, waxes, emulsifiers, higher alcohols, fatty acids, silicon oils, surfactants, phospholipids, alcohols, polyhydric alcohols, water-soluble polymers, clay minerals and purified water.

These external preparations can each contain usually 0.000001 to 99.5% by weight, preferably 0.00001 to 90% by weight or the like, of a compound of the formula (I) or a pharmaceutically acceptable salt thereof.

The dosage of the salt of compound (I) or the crystal thereof varies depending on the extent of the symptom, age, gender, body weight, dosage form, the type of the salt, the specific type of the disease and the like. In the case of adults, typically, about 30 μg to 10 g, preferably 100 μg to 5 g, and more preferably 100 μg to 1 g per day is orally administered, or about 30 μg to 1 g, preferably 100 μg to 500 mg, and more preferably 100 μg to 300 mg per day is administered by injection, in each case, in a single dose or in divided doses.

EXAMPLE

The present invention will be described in detail below by showing Reference Examples and Examples, but is not limited by these Reference Examples and Examples.

The following abbreviations will be used in Examples and Reference Examples in the present specification.
CDI: 1,1'-carbonyldiimidazole
DCM: dichloromethane
DMF-DMA: N,N-dimethylformamide dimethyl acetal
DMF: N,N-dimethylformamide
DMSO: dimethylsulfoxide
DTT: dithiothreitol
IPA: isopropyl alcohol
KTB: potassium tert-butoxide
MTBE: t-butylmethylether
NBS: N-bromosuccinimide
Pd(dppf)Cl$_2$ DCM complex: [1,1'-bis(diphenylphosphine)ferrocene]dichloropalladium(II) DCM complex
Pd(PPh$_3$)$_4$: tetrakis(triphenylphosphine)palladium(0)
TEA: triethylamine
TFA: trifluoroacetic acid
THF: tetrahydrofuran
Tris: trishydroxymethylaminomethane The chemical shift of the proton nuclear magnetic resonance spectrum is recorded in δ units (ppm) from tetramethylsilane; and the coupling constant is recorded in hertz (Hz). The abbreviations of splitting patterns are as follows: s: singlet, d: doublet, t: triplet, q: quartet, m: multiplet, brs: broad singlet and brd: broad doublet.

In powder X-ray crystal diffraction of the crystals produced in Examples below, the obtained crystals were mounted on the sample stage of a powder X-ray diffraction apparatus and analyzed under the following conditions.
Measurement Conditions
Sample holder: aluminum
Target: copper
Detector: scintillation counter
Tube voltage: 50 kV
Tube current: 300 mA
Slit: DS 0.5 mm (Height limiting slit 2 mm), SS Open, RS Open
Scanning rate: 10°/min
Sampling interval: 0.02°
Scan range: 5 to 35°
Goniometer: horizontal goniometer The $^{13}$C solid-state NMR spectra of the crystals were measured under the following conditions.
Measurement Conditions
Apparatus used: AVANCE400 (from Bruker Corporation)
Measurement temperature: room temperature (22° C.)
Reference material: glycine (external reference: 176.03 ppm)
Measured nucleus: $^{13}$C (100.6248425 MHz)
Pulse repetition time: 3 seconds
Pulse mode: TOSS measurement Reference Example 1

Synthesis of (S)-7-(2-methoxy-3,5-dimethylpyridin-4-yl)-1-(tetrahydrofuran-3-yl)-1H-pyrazolo[4,3-c]quinolin-4(5H)-one

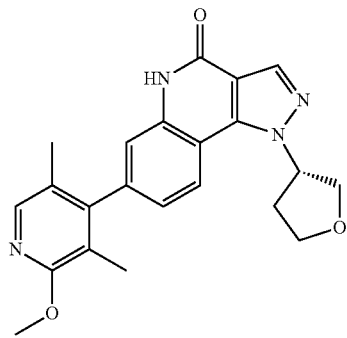

(I)

(1) Synthesis of benzyl 2-[dihydrofuran-3(2H)-ylidene]hydrazinecarboxylate 3-oxotetrahydrofuran (5.70 g) was dissolved in methanol (150 mL), and benzyl carbazate (10 g) was added to the solution. The mixture was stirred at room temperature for 12 hours. The reaction mixture was concentrated. 14.8 g of a residue was obtained as a crude product. This was used for the next reaction without further purification.

(2) Synthesis of (±)-benzyl 2-(tetrahydrofuran-3-yl)hydrazinecarboxylate

Benzyl 2-[dihydrofuran-3(2H)-ylidene]hydrazinecarboxylate (14.8 g) was suspended in water (96 mL). Acetic acid (42.1 mL) was added to the suspension at room temperature. The mixture was stirred at room temperature for one hour. The suspension turned into a solution. Sodium cyanoborohydride (4.0 g) was added to the solution in small portions. The mixed solution was stirred at room temperature for two hours. The reaction mixture was cooled to 0° C. The reaction mixture was neutralized by adding a 5 N aqueous sodium hydroxide solution. The mixture was extracted with chloroform. The organic layer was dried over anhydrous magnesium sulfate and then filtered. The filtrate was concentrated under reduced pressure. The residue was purified by silica gel column chromatography (methanol/ethyl acetate, 5%). The title compound (13.9 g) was obtained.

$^1$H-NMR (400 MHz, CDCl$_3$) δ (ppm): 1.73-1.80 (m, 1H), 1.92-2.06 (m, 1H), 3.66-3.82 (m, 3H), 3.82-4.03 (m, 2H), 5.14 (s, 2H), 7.31-7.40 (m, 5H).

(3) Synthesis of (−)-benzyl 2-(tetrahydrofuran-3-yl)hydrazinecarboxylate and (+)-benzyl 2-(tetrahydrofuran-3-yl)hydrazinecarboxylate A saturated aqueous sodium bicarbonate solution (30 mL) was added to a solution of (±)-benzyl 2-(tetrahydrofuran-3-yl)hydrazinecarboxylate (11.5 g) in MTBE (110 mL). The mixture was stirred for 10 minutes at room temperature, and the organic layer was then separated. The resulting organic layer was sequentially washed with saturated sodium bicarbonate and brine and dried over anhydrous magnesium sulfate, and the desiccant was removed by filtration. The filtrate was concentrated under reduced pressure. The resulting residue was purified by silica gel column chromatography (ethyl acetate/hexane, 25 to 50%), and the target fraction was concentrated. Diethyl ether (30 mL) and hexane (15 mL) were added to the residue. The precipitated solid was collected by filtration and dried under reduced pressure to give pure (±)-benzyl 2-(tetrahydrofuran-3-yl)hydrazinecarboxylate (6.17 g).

This product was dissolved in ethanol and filtered through a millipore filter. The resulting filtrate was optically resolved under two conditions.
Condition 1: CHIRALCEL™ made by DAICEL Corp., OD-H (20 mmΦ×250 mm L), 20% IPA-hexane, 25 mL/min.
Condition 2: CHIRALPAK™ made by DAICEL Corp., AD-H (20 mmΦ×250 mm L), 20% IPA-hexane, 24 mL/min.
The target fraction was concentrated to give the title compound with a short retention time and a 0 optical rotation (2.60 g, >99% ee [OD-H, 20% IPA/hexane, retention time=11.2 min]), and the title compound with a long retention time and a (+) optical rotation (2.59 g, 97.2% ee [OD-H, 20% IPA/hexane, retention time=12.4 min]).

(4) Synthesis of (S)-tetrahydrofuran-3-yl)hydrazine hydrochloride (−)-Benzyl 2-(tetrahydrofuran-3-yl)hydrazinecarboxylate (50 g) was dissolved in methanol (500 mL), and di-t-butyl dicarbonate (92.4 g) and palladium carbon (50% wet) (5 g) were added. The mixture was stirred at 25° C. and 15 psi for 48 hours in a hydrogen atmosphere. The reaction mixture was filtered, and the filtrate was concentrated under reduced pressure. The resulting residue was dissolved in diisopropyl ether (300 mL). After cooling at 0° C., hydrochloric acid/diisopropyl ether (500 mL) was added to the solution. The mixture was stirred at 10° C. for 14 hours. The precipitated solid was collected by filtration. The same operation from (−)-benzyl 2-(tetrahydrofuran-3-yl)hydrazinecarboxylate (70 g) was performed nine times, and the same operation from (−)-benzyl 2-(tetrahydrofuran-3-yl)hydrazinecarboxylate (50 g) was performed once. The resulting solid was triturated with DCM/ethanol (10/1) (1 L) for two hours. The precipitated solid was collected by filtration. The resulting solid was dried under reduced pressure to give the title compound (235 g).

$^1$H-NMR (400 MHz, DMSO-d$_6$) δ (ppm): 1.87-2.09 (m, 2H), 3.55-3.71 (m, 2H), 3.71-3.84 (m, 3H).

The absolute configuration of the resulting title compound was confirmed to be an (S)-form according to X-ray crystallography.

(5) Synthesis of 2-Fluoro-3-iodo-5-methylpyridine

Diisopropylamine (92 mL) was added to THF (1.2 L), and the mixture was cooled to −18° C. under a nitrogen atmosphere. To this solution was added dropwise a solution (224 mL) of 2.69 M n-butyllithium in hexane. After the dropwise addition, the temperature was increased to −5° C. over 20 minutes while stirring this mixture. The reaction solution was cooled to −73° C. To this reaction solution was added dropwise a THF solution (240 mL) of 2-fluoro-5-methylpyridine (61 g). The reaction mixture was stirred at −75° C. for three and a half hours. To this reaction solution was added dropwise a THF solution (24 mL) of iodine (139 g). The reaction mixture was stirred at −75° C. for 1 hour and 55 minutes. After the reaction, water (220 mL) was added to the reaction solution at the same temperature. The mixture was stirred at the same temperature for 5 minutes. The reaction solution was brought back to room temperature, and then water (1.2 L) was added. To this mixture were added an aqueous solution (300 mL) of sodium thiosulfate pentahydrate (136 g) and water (300 mL), and the mixture was stirred for 10 minutes. This mixture was extracted with MTBE (1.2 L). The organic layer was washed with saturated saline (500 mL). The combined aqueous layers were extracted with MTBE (1 L). The combined organic layers were dried over anhydrous magnesium sulfate. The drying agent was removed by filtration and the filtrate was concentrated under reduced pressure. n-Heptane was added to the residue, and the mixture was cooled. The precipitated solid was collected by filtration. The solid was washed with n-heptane. The filtrate was cooled, and the precipitated solid was collected by filtration. The procedure was repeated 5 times to give the title compound (109.69 g).

$^1$H-NMR (400 MHz, CDCl$_3$) δ (ppm): 2.29-2.31 (m, 3H), 7.93-8.14 (m, 2H).
ESI-MS m/z 238 [M+H]$^+$ (6) Synthesis of 2-Fluoro-4-iodo-3,5-dimethylpyridine Diisopropylamine (88 ml) was added to THF (1.2 L), and the mixture was cooled to −18° C. under a nitrogen atmosphere. To this solution was added dropwise a solution (215 mL) of 2.69 M n-butyllithium in hexane. After the dropwise addition, the temperature was increased to −5° C. over 30 minutes while stirring this mixture. The reaction solution was cooled to −72° C. To this reaction solution was added dropwise a THF solution (240 mL) of 2-Fluoro-3-iodo-5-methylpyridine (109.69 g). The reaction mixture was stirred at −74° C. for one and a half hours. To this reaction solution was added dropwise a THF solution (160 mL) of methyl iodide (36 ml). The reaction mixture was stirred at −70° C. to −74° C. for 2 hours. After the reaction, water (200 mL) was added to the reaction solution at the same temperature. The mixture was stirred at the same temperature for 2 minutes. The reaction solution was brought back to room temperature, and then water (1.2 L) was added. This mixture was stirred for 3 minutes. Water (300 mL) was further added. This mixture was extracted with MTBE (1.2 L). The organic layer was washed with saturated saline (500 mL). The combined aqueous layers were extracted with MTBE (1 L). The combined organic layers were dried over anhydrous magnesium sulfate. The drying agent was removed by filtration and the filtrate was concentrated under reduced pressure. n-Heptane (100 mL) was added to the residue, and the mixture cooled. The precipitated solid was collected by filtration. The solid was washed with n-heptane. The filtrate was cooled, and the precipitated solid was collected by filtration. The procedure was repeated twice to give the title compound (86.9 g).

$^1$H-NMR (400 MHz, CDCl$_3$) δ (ppm): 2.39-2.40 (m, 6H), 7.80-7.82 (m, 1H).

ESI-MS m/z 252 [M+H]$^+$ (7) Synthesis of
4-Iodo-2-methoxy-3,5-dimethylpyridine

To a THF (954 mL) solution of 2-Fluoro-4-iodo-3,5-dimethylpyridine (97.4 g) was added, at 20° C., a methanol solution (185 mL) of 28% sodium methoxide. This mixture was stirred at 55° C. to 65° C. for 2 hours. The reaction solution was cooled, and then separated by adding MTBE (1 L) and water (1 L). The organic layer was washed with saturated saline. The combined aqueous layers were extracted with MTBE (500 mL×2). The combined organic layers were dried over anhydrous magnesium sulfate. The drying agent was removed by filtration and the filtrate was concentrated under reduced pressure. n-Heptane (50 mL) was added to the residue, and the mixture was stirred at 0° C. for 1 hour. The precipitated solid was collected by filtration. The solid was washed with chilled n-heptane (10 mL). The title compound (42.6 g) was obtained. The filtrate was concentrated under reduced pressure. n-Heptane (5 mL) was added to the residue, and the mixture was stirred at 0° C. for 30 minutes. The precipitated solid was collected by filtration. The solid was washed with chilled n-heptane (2 mL) to give the title compound (20.2 g). The filtrate was concentrated under reduced pressure. n-Heptane (5 mL) was added to the residue, and the mixture was stirred at 0° C. for 30 minutes. The precipitated solid was collected by filtration. The solid was washed with chilled n-heptane (2 mL). The title compound (10.7 g) was obtained. When combined, the title compound (73.5 g) was obtained.

$^1$H-NMR (400 MHz, CDCl$_3$) δ (ppm): 2.33-2.34 (m, 3H), 2.36-2.38 (m, 3H), 3.92 (s, 3H), 7.76 (s, 1H).

ESI-MS m/z 264 [M+H]$^+$ (8) Synthesis of Ethyl
3-(4-bromo-2-fluorophenyl)-3-oxopropanoate CDI (8.88 g) was added to a suspension of 4-bromo-2-fluorobenzoic acid (CAS No. 112704-79-7) (10 g) in DCM (97 mL), and the mixture was stirred at room temperature for 3.5 hours. This solution is referred to as "solution 1".

To a suspension of potassium ethyl malonate (15.5 g) in acetonitrile (303 mL) in another flask was added TEA (15.9 mL) and then magnesium chloride (10.9 g), and the mixture was stirred at room temperature for 3 hours and 10 minutes. To this reaction mixture was added, dropwise over 25 minutes, the "solution 1" prepared above, and then the reaction mixture was stirred at room temperature overnight. The reaction solution was concentrated to half the volume under reduced pressure. The obtained residue was diluted in ethyl acetate (500 mL), and after addition of 5N hydrochloric acid (250 mL) under ice-cooling was stirred at room temperature for 1 hour. The organic layer was separated. The organic layer was washed with saturated saline, dried over anhydrous magnesium sulfate, filtered and concentrated under reduced pressure. The obtained residue was purified by column chromatography on silica gel (ethyl acetate/n-heptane, 5-20%) to give the title compound (12.8 g).

ESI-MS m/z 291 [M+H]$^+$ (9) Synthesis of Ethyl 5-(4-bromo-2-fluorophenyl)-1-[(S)-tetrahydrofuran-3-yl]-1H-pyrazole-4-carboxylate A solution of ethyl 3-(4-bromo-2-fluorophenyl)-3-oxopropanoate (45 g) in DMF-DMA (165 mL) was stirred at 50° C. for 2 hours and 15 minutes. The reaction solution was concentrated under reduced pressure. Toluene (200 mL) was added to the residue, and the mixture was concentrated under reduced pressure again. Ethanol (950 mL) was added to the residue, and the mixture was heated to 50° C. To the solution was added, dropwise over 35 minutes, an aqueous solution (60 mL) of (S)-(tetrahydrofuran-3-yl)hydrazine hydrochloride (21.6 g). The obtained reaction mixture was stirred at 50° C. for 2 hours and 10 minutes. The reaction solution was cooled to room temperature and then concentrated to half the volume under reduced pressure. Water (200 mL) was added to the residue, and ethanol was distilled off under reduced pressure. Ethyl acetate (500 mL) was added to the obtained residue, and the organic layer was separated. The aqueous layer was extracted with ethyl acetate (100 mL). The combined organic layers were washed with saturated saline, dried over anhydrous magnesium sulfate, filtered and concentrated under reduced pressure. The residue was purified by column chromatography on silica gel (ethyl acetate/n-heptane, 10% to 15%) and then by short-path column chromatography on NH silica gel (propylamine-coated silica gel from Fuji Silysia Chemical Ltd.) (ethyl acetate/n-heptane, 33%) to give the title compound (43.1 g).

$^1$H-NMR (400 MHz, CDCl$_3$) δ (ppm): 1.19 (t, J=7.2 Hz, 3H), 2.19-2.49 (m, 2H), 3.87-4.07 (m, 3H), 4.11-4.25 (m, 3H), 4.58-4.65 (m, 1H), 7.17-726 (m, 1H), 7.39-7.47 (m, 2H), 8.06 (s, 1H).

ESI-MS m/z 407 [M+Na]$^+$

(10) Synthesis of Ethyl 5-[2-fluoro-4-(4,4,5,5-tetramethyl-1,3,2-dioxaborolan-2-yl)phenyl]-1-[(S)-tetrahydrofuran-3-yl]-1H-pyrazole-4-carboxylate A mixture of ethyl 5-(4-bromo-2-fluorophenyl)-1-[(S)-tetrahydrofuran-3-yl]-1H-pyrazole-4-carboxylate (43.1 g), bis(pinacolato)diboron (34.3 g), Pd(dppf)Cl$_2$ DCM complex (4.59 g) and potassium acetate (33.1 g) was dried under reduced pressure using a vacuum pump for 1 hour. A solution of the dried residue in DMF (430 mL) was stirred at 80° C. for 3 hours and 10 minutes. The reaction solution was brought back to room temperature and then filtered through Celite™. The filtrate was concentrated under reduced pressure. To the residue was added ethyl acetate (430 mL) and saturated saline (200 mL), and the mixture was stirred for 5 minutes. The insoluble matter was removed by filtration using Celite™. The organic layer was separated from the filtrate. The aqueous layer was again extracted with ethyl acetate (50 mL). The combined organic layers were dried over anhydrous magnesium sulfate and filtered, and the filtrate was concentrated under reduced pressure. The residue was purified by column chromatography on silica gel (ethyl acetate/n-heptane, 10-15%) to give the title compound (51.9 g).

$^1$H-NMR (400 MHz, CDCl$_3$) δ (ppm): 1.16 (t, J=7.2 Hz, 3H), 1.37 (s, 12H), 2.15-2.49 (m, 2H), 3.85-4.06 (m, 3H), 4.14 (q, J=7.2 Hz, 2H), 4.20 (dd, J=15.6, 8.4 Hz, 1H), 4.57-4.66 (m, 1H), 7.30 (t, J=7.2 Hz, 0.5H), 7.35 (t, J=7.2 Hz, 0.5H), 7.63 (dd, J=5.6, 2.0 Hz, 1H), 7.70 (dd, J=7.2, 2.0 Hz, 1H), 8.06 (s, 1H).

(11) Synthesis of ethyl 5-[2-fluoro-4-(2-methoxy-3,5-dimethylpyridin-4-yl)phenyl]-1-[(S)-tetrahydrofuran-3-yl]-1H-pyrazole-4-carboxylate Water (170 mL), 4-iodo-2-methoxy-3,5-dimethylpyridine (35.6 g), Pd(PPh$_3$)$_4$ (6.52 g) and cesium carbonate (110 g) were added to a solution of ethyl 5-[2-fluoro-4-(4,4,5,5-tetramethyl-1,3,2-dioxaborolan-2-yl)phenyl]-1-[(S)-tetrahydrofuran-3-yl]-1H-pyrazole-4-carboxylate (51.9 g) in 1,4-dioxane (500 mL), and the reaction mixture was reacted at 110° C. for six hours. The reaction mixture was returned to room temperature, and the organic layer was then separated. The organic layer was concentrated under reduced pressure. The aqueous layer, ethyl acetate (700 m) and water (100 mL) were added to the resulting residue, and the organic layer was separated. The aqueous layer was re-extracted with ethyl acetate (50 mL). The combined organic layers were sequentially washed with water and brine, dried over anhydrous magnesium sulfate, filtered and concentrated under reduced pressure. The residue was purified by NH silica gel column chromatography (ethyl acetate/n-heptane, 5% to 14%). The product was then purified again by NH silica gel column chromatography (ethyl acetate/n-heptane, 2% to 10%) to give the title compound (43.5 g).

$^1$H-NMR (400 MHz, CDCl$_3$) δ (ppm): 1.16 (t, J=7.2 Hz, 1.5H), 1.17 (t, J=7.2 Hz, 1.5H), 1.97 (s, 1.5H), 1.98 (s, 1.5H), 1.99 (s, 1.5H), 2.00 (s, 1.5H), 2.25-2.55 (m, 2H), 3.92-4.27 (m, 6H), 3.99 (s, 1.5H), 4.00 (s, 1.5H), 4.65-4.75 (m, 1H), 7.01 (d, J=9.2 Hz, 1H), 7.05 (d, J=7.2 Hz, 1H), 7.39 (t, J=7.2 Hz, 0.5H), 7.45 (t, J=7.2 Hz, 0.5H), 7.93 (s, 1H), 8.12 (s, 1H).

ESI-MS m/z 440 [M+H]$^+$

(12) Synthesis of 5-[2-fluoro-4-(2-methoxy-3,5-dimethylpyridin-4-yl)phenyl]-1-[(S)-tetrahydrofuran-3-yl]-1H-pyrazole-4-carboxylic acid A 5 N aqueous sodium hydroxide solution (79 mL) was added to a solution of ethyl 5-[2-fluoro-4-(2-methoxy-3,5-dimethylpyridin-4-yl)phenyl]-1-[(S)-tetrahydrofuran-3-yl]-1H-pyrazole-4-carboxylate (43.2 g) in ethanol (574 mL) at room temperature, and the reaction mixture was stirred at 60° C. for two hours and 10 minutes. The reaction mixture was cooled to room temperature and then concentrated to half volume under reduced pressure. Water (300 mL) was added to the residue, and ethanol was distilled off under reduced pressure. MTBE (130 mL) was added to the resulting residue, and the aqueous layer was separated. The organic layer was extracted with water (30 mL). The combined aqueous layers were made acidic with 5 N hydrochloric acid (78 mL) under ice-cooling and extracted with ethyl acetate twice. The combined organic layers were dried over anhydrous magnesium sulfate, filtered and concentrated under reduced pressure to give the title compound (39.0 g).

$^1$H-NMR (400 MHz, CDCl$_3$) δ (ppm): 1.91 (s, 1.5H), 1.94 (s, 1.5H), 1.98 (s, 1.5H), 2.01 (s, 1.5H), 2.25-2.56 (m, 2H), 3.92-4.17 (m, 3H), 3.96 (s, 1.5H), 4.00 (s, 1.5H), 4.23 (dd, J=16.0, 8.0 Hz, 1H), 4.65-4.77 (m, 1H), 6.99 (brd, J=10.0 Hz, 1H), 7.03 (dr d, J=7.6 Hz, 1H), 7.38 (t, J=7.6 Hz, 0.5H), 7.44 (t, J=7.6 Hz, 0.5H), 7.90 (s, 0.5H), 7.94 (s, 0.5H), 8.14 (s, 1H).

ESI-MS m/z 434 [M-Na]$^+$

(13) Synthesis of 5-[2-fluoro-4-(2-methoxy-3,5-dimethylpyridin-4-yl)phenyl]-1-[(S)-tetrahydrofuran-3-yl]-1H-pyrazole-4-carboxamide CDI (21.4 g) was added at one time to a solution of 5-[2-fluoro-4-(2-methoxy-3,5-dimethylpyridin-4-yl)phenyl]-1-[(S)-tetrahydrofuran-3-yl]-1H-pyrazole-4-carboxylic acid (38.7 g) in DMF (290 mL) at room temperature, and the mixture was stirred at room temperature for 95 minutes. 28% aqueous ammonia (95 mL) was added to the reaction mixture, and the mixture was stirred at room temperature for 35 minutes. 28% aqueous ammonia (95 mL) was added again to the reaction mixture, and the mixture was stirred at room temperature for 90 minutes. The reaction mixture was concentrated under reduced pressure. Chloroform (250 mL) and water (80 mL) were added to the resulting residue, and the organic layer was separated. The aqueous layer was re-extracted with chloroform (50 mL). The combined organic layers were sequentially washed with a saturated aqueous ammonium chloride solution (60 mL×3) and brine, dried over anhydrous magnesium sulfate and filtered. The filtrate was passed through a silica pad (NH-silica gel). The filtrate was concentrated under reduced pressure to give the title compound (37.2 g).

$^1$H-NMR (400 MHz, CDCl$_3$) δ (ppm): 1.98 (brs, 6H), 2.24-2.60 (m, 2H), 3.90-4.20 (m, 3H), 3.99 (s, 3H), 4.23 (dd, J=16.0, 8.0 Hz, 1H), 4.62-4.71 (m, 1H), 5.32 (brs, 2H), 7.05 (brd, J=10.0 Hz, 1H), 7.10 (dd, J=7.6, 1.2 Hz, 1H), 7.42-7.56 (m, 1H), 7.94 (brs, 1H), 8.03 (s, 1H).

ESI-MS m/z 411 [M+H]$^+$

(14) Synthesis of (S)-7-(2-methoxy-3,5-dimethylpyridin-4-yl)-1-(tetrahydrofuran-3-yl)-1H-pyrazolo[4,3-c]quinolin-4(5H)-one Sodium hydroxide powder (9.43 g) was added at one time to a solution of 5-[2-fluoro-4-(2-methoxy-3,5-dimethylpyridin-4-yl)phenyl]-1-[(S)-tetrahydrofuran-3-yl]-1H-pyrazole-4-carboxamide (37.2 g) in DMSO (186 mL) at room temperature. The reaction mixture was stirred at the same temperature for 50 minutes and then at 70° C. for 45 minutes. Under water-cooling, water (600 mL) was added dropwise to the reaction mixture, and then acetic acid (13.5 mL) was added dropwise. The precipitated powder was collected by filtration. The collected subject was washed with water and MTBE and then dried under reduced pressure to give the title compound (34.0 g).

$^1$H-NMR (400 MHz, CDCl$_3$) δ (ppm): 1.92-1.94 (m, 3H), 1.94-1.96 (m, 3H), 2.55-2.66 (m, 1H), 2.76-2.86 (m, 1H), 4.00 (s, 3H), 4.09-4.16 (m, 1H), 4.24-4.37 (m, 2H), 4.39-4.45 (m, 1H), 5.61-5.68 (m, 1H), 7.04 (d, J=1.5 Hz, 1H), 7.08 (dd, J=1.5 Hz, 8.3 Hz, 1H), 7.94 (s, 1H), 8.13 (d, J=8.3 Hz, 1H), 8.31 (s, 1H), 8.86 (s, 1H).

ESI-MS m/z 391 [M+H]$^+$

The title compound showed an optical rotation of (−), and its optical purity was ≥99% ee[AD-H, 100% ethanol, retention time: 9.7 min].

Reference Example 2

Synthesis of (−)-7-(2-methoxy-3,5-dimethylpyridin-4-yl)-1-(tetrahydrofuran-3-yl)-1H-pyrazolo[4,3-c]quinolin-4(5H)-one

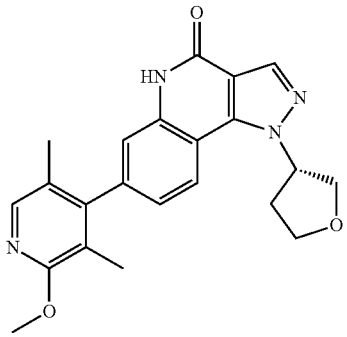

(I)

Synthesis of (±)-5-(2,4-dimethoxybenzyl)-1-(tetrahydrofuran-3-yl)-7-(4,4,5,5-tetramethyl-1,3,2-dioxaborolan-2-yl)-1H-pyrazolo[4,3-c]quinolin-4(5H)-one (1) Synthesis of ethyl 3-(4-bromo-2-chlorophenyl)-3-oxopropionate 4-Bromo-2-chlorobenzoic acid (1 g) was suspended in DCM (10 mL). CDI (960 mg) was added to the resultant suspension, and stirred at room temperature for 4 hours. The solution is taken as "Solution 1". Potassium ethyl malonate (1.1 g) was suspended in acetonitrile (20 mL) in another flask in a nitrogen atmosphere, and TEA (1.5 mL) was added. The resultant solution was cooled to 0° C., and magnesium chloride (805 mg) was added little by little, and thereafter stirred at room temperature for 2 hours. The reaction mixture was cooled to 0° C., and "Solution 1" prepared in the above was dropped therein. After the completion of the dropping, the reaction mixture was stirred at room temperature for 17 hours. The reaction mixture was further stirred at 50° C. for 9 hours. The reaction mixture was concentrated under reduced pressure and the DCM was removed. The obtained residue was cooled to 0° C., and ethyl acetate (50 mL) and a 2N hydrochloric acid (20 mL) were added, and stirred at room temperature for 1 hour. The resultant organic layer was partitioned. The resultant water layer was extracted with ethyl acetate. The extract was combined with the organic layer, and dried with anhydrous magnesium sulfate. The desiccant was removed by filtration, and the filtrate was concentrated under reduced pressure. The obtained residue was purified by silica gel column chromatography (ethyl acetate/n-heptane, 0% to 10%) to thereby obtain the title compound (1.2 g).

ESI-MS m/z 307 [M+H]$^+$ (2) Synthesis of (±)-ethyl 5-(4-bromo-2-chlorophenyl)-1-(tetrahydrofuran-3-yl)-1H-pyrazole-4-carboxylate Ethyl 3-(4-bromo-2-chlorophenyl)-3-oxopropanoate (2.00 g) was dissolved in DMF-DMA (6.96 mL), and the reaction mixture was stirred at room temperature for 1.5 hours. The reaction mixture was concentrated under reduced pressure, and the residue was dissolved in ethanol (40 mL). (±)-(Tetrahydrofuran-3-yl)hydrazine hydrochloride (998 mg) was added to the solution, and the mixture was heated under reflux for two hours. The reaction mixture was cooled to room temperature and then concentrated under reduced pressure. The residue was extracted with ethyl acetate, and the organic layer was purified by silica gel column chromatography (ethyl acetate/n-heptane, 10% to 30%) to give the title compound (1.05 g).

ESI-MS m/z 401 [M+H]$^+$ (3) Synthesis of (±)-5-(4-bromo-2-chlorophenyl)-1-(tetrahydrofuran-3-yl)-1H-fura-pyrazole-4-carboxylic acid A mixture of (±)-ethyl 5-(4-bromo-2-chlorophenyl)-1-(tetrahydrofuran-3-yl)-1H-pyrazole-4-carboxylate (1.05 g) and a 5 N aqueous sodium hydroxide solution (1.58 mL) was stirred in a mixed solvent of ethanol (20 mL) and water (5 mL) at 60° C. for three hours. The reaction mixture was cooled to room temperature and then concentrated under reduced pressure. 5 N hydrochloric acid was added to the residue, followed by extraction with ethyl acetate. The organic layer was dried over anhydrous magnesium sulfate, and the desiccant was filtered off. The filtrate was concentrated under reduced pressure to give the title compound (1 g).

ESI-MS m/z 371 [M+H]$^+$ (4) Synthesis of (±)-5-(4-bromo-2-chlorophenyl)-N-(2,4-dimethoxybenzyl)-1-(tetrahydrofuran-3-yl)-1H-pyrazole-4-carboxamide (±)-5-(4-bromo-2-chlorophenyl)-1-(tetrahydrofuran-3-yl)-1H-pyrazole-4-carboxylic acid (1 g) was dissolved in DCM (20 mL), and CDI (611 mg) was added, followed by stirring at room temperature for one hour. 2,4-dimethoxybenzylamine (0.809 mL) was added to the reaction mixture, and the mixture was stirred at room temperature for two hours. A saturated aqueous sodium bicarbonate solution was added to the reaction mixture, followed by extraction with DCM. The organic layer was concentrated under reduced pressure, and the residue was purified by silica gel column chromatography (ethyl acetate/n-heptane, 10% to 40%) to give the title compound (1.26 g).

ESI-MS m/z 522 [M+H]$^+$ (5) Synthesis of (±)-7-bromo-5-(2,4-dimethoxybenzyl)-1-(tetrahydrofuran-3-yl)-1H-pyrazolo[4,3-c]quinolin-4(5H)-one (±)-5-(4-bromo-2-chlorophenyl)-N-(2,4-dimethoxybenzyl)-1-(tetrahydrofuran-3-yl)-1H-pyrazole-4-carboxamide (1.26 g) was dissolved in THF (25 mL), and KTB (597 mg) was added at 0° C. The mixture was stirred for 12 hours while gradually warming to room temperature. The reaction mixture was cooled to 0° C., and water was added, followed by filtration. The filtration residue was separately stored. The filtrate was extracted with ethyl acetate, and the organic layer was concentrated under reduced pressure. The residue was purified by silica gel column chromatography (ethyl acetate/n-heptane, 10% to 70%). The resulting fraction and the filtration residue obtained above were combined and concentrated to give the title compound (488 mg).

$^1$H-NMR (400 MHz, CDCl$_3$) δ (ppm): 2.50-2.62 (m, 1H), 2.72-2.82 (m, 1H), 3.76 (s, 3H), 4.02 (s, 3H), 4.07-4.15 (m, 1H), 4.19-4.32 (m, 2H), 4.35-4.42 (m, 1H), 5.46-5.57 (m, 3H), 6.34 (dd, J=8.6 Hz, 2.2 Hz, 1H), 6.52 (d, J=2.2 Hz, 1H), 6.99 (d, J=8.6 Hz, 1H), 7.38 (dd, J=8.6 Hz, 1.8 Hz, 1H), 7.82 (d, J=1.8 Hz, 1H), 7.89 (d, J=8.6 Hz, 1H), 8.32 (s, 1H).
ESI-MS m/z 506 [M+Na]$^+$ (6) Synthesis of (±)-5-(2,4-dimethoxybenzyl)-1-(tetrahydrofuran-3-yl)-7-(4,4,5,5-tetramethyl-1,3,2-dioxaborolan-2-yl)-1H-pyrazolo[4,3-c]quinolin-4(5H)-one A mixture of (±)-7-bromo-5-(2,4-dimethoxybenzyl)-1-(tetrahydrofuran-3-yl)-1H-pyrazolo[4,3-c]quinolin-4(5H)-one (300 mg), bis(pinacolato)diboron (204 mg), Pd(dppf)Cl$_2$-DCM complex (13.6 mg) and potassium acetate (182 mg) was reacted in a mixed solvent of 1,4-dioxane (15 mL) and DMSO (1 mL) using a microwave reactor at 130° C. for three hours. The reaction mixture was cooled to room temperature and then concentrated under reduced pressure. The residue was extracted with ethyl acetate, and the organic layer was concentrated under reduced pressure. The residue was subjected to a silica gel pad and eluted with ethyl acetate to give the title compound (428 mg) as a crude product.
ESI-MS m/z 532 [M+H]$^+$ (7) Synthesis of 3,5-dibromo-2-methoxypyridin-4-amine A mixture of 2-methoxy-pyridin-4-ylamine (15 g) and NBS (47.3 g) was stirred in an acetic acid solvent (150 mL) at room temperature for three hours. The reaction mixture was concentrated under reduced pressure, and a 5 N aqueous sodium hydroxide solution (200 mL) was added to the residue at 0° C., followed by extraction with diethyl ether. The organic layer was directly purified by a silica gel pad (ethyl acetate/n-heptane, 10%) to give the title compound (32.4 g).
ESI-MS m/z 283 [M+H]$^+$ (8) Synthesis of 2-methoxy-3,5-dimethylpyridin-4-amine A mixture of 3,5-dibromo-2-methoxypyridine-4-amine (16 g), trimethylboroxin (19.8 mL), Pd(dppf)Cl$_2$-DCM complex (4.15 g) and potassium carbonate (23.5 g) was heated under reflux in a mixed solvent of 1,4-dioxane (320 mL) and water (32 mL) for 12 hours. The reaction mixture was cooled to room temperature and then concentrated under reduced pressure. Water and ethyl acetate were added to the residue, followed by filtration through Celite™. The filtrate was extracted with ethyl acetate, and the organic layer was subjected to a silica gel pad (NH-silica gel) and eluted with ethyl acetate. NH-silica gel (30 g) was added to the resulting solution, and the mixture was concentrated under reduced pressure. The residue was purified by NH silica gel column chromatography (ethyl acetate/n-heptane, 0% to 30%) to give the title compound (4.43 g).
ESI-MS m/z 153 [M+H]$^+$ (9) Synthesis of 4-bromo-2-methoxy-3,5-dimethylpyridine A mixture of copper(I) bromide (12.1 g) and t-butyl nitrite (7.07 mL) was stirred in an acetonitrile solvent (80 mL) at 70° C. for 10 minutes. A solution of 2-methoxy-3,5-dimethylpyridin-4-amine (3.9 g) in acetonitrile (40 mL) was added dropwise to the reaction mixture at the same temperature, and the mixture was stirred at 70° C. for one hour. The reaction mixture was cooled to room temperature and then concentrated under reduced pressure. Ethyl acetate and a saturated aqueous sodium bicarbonate solution were added to the residue, and the mixture was stirred at room temperature for 30 minutes. The reaction mixture was filtered through Celite™, and the filtrate was extracted with ethyl acetate. The organic layer was concentrated under reduced pressure, and the residue was purified by NH silica gel column chromatography (n-heptane, 100%, then NH-silica gel pad, n-heptane, 100%) to give the title compound (4.3 g).
$^1$H-NMR (400 MHz, CDCl$_3$) δ (ppm): 2.28-2.29 (m, 3H), 2.29-2.31 (m, 3H), 3.93 (s, 3H), 7.77-7.84 (m, 11-1).
ESI-MS m/z 216 [M+H]$^+$

(10) Synthesis of (±)-7-(2-methoxy-3,5-dimethylpyridin-4-yl)-1-(tetrahydrofuran-3-yl)-1H-pyrazolo[4,3-c]quinolin-4(5H)-one A mixture of (±)-5-(2,4-dimethoxybenzyl)-1-(tetrahydrofuran-3-yl)-7-(4,4,5,5-tetramethyl-1,3,2-dioxaborolan-2-yl)-1H-pyrazolo[4,3-c]quinolin-4(5H)-one (219 mg), 4-bromo-2-methoxy-3,5-dimethylpyridine (134 mg), Pd(PPh$_3$)$_4$ (23.8 mg) and cesium carbonate (403 mg) was reacted in a mixed solvent of 1,4-dioxane (8 mL) and water (2 mL) using a microwave reactor at 130° C. for 70 minutes. The reaction mixture was cooled to room temperature and then directly purified by silica gel column chromatography (ethyl acetate/n-heptane, 10% to 90%). The resulting coupling product was dissolved in TFA (4 mL), and the mixture was stirred at 70° C. for two hours. The reaction mixture was cooled to room temperature and then concentrated under reduced pressure. A saturated aqueous sodium bicarbonate solution was added to the residue, followed by extraction with ethyl acetate. The organic layer was concentrated under reduced pressure, and the residue was purified by silica gel column chromatography (DCM, 100%, then ethyl acetate/n-heptane, 50% to 100%) to give the title compound (78 mg).
ESI-MS m/z 391 [M+H]$^+$

(11) Synthesis of (+)-7-(2-methoxy-3,5-dimethylpyridin-4-yl)-1-(tetrahydrofuran-3-yl)-1H-pyrazolo[4,3-c]quinolin-4(5H)-one and (−)-7-(2-methoxy-3,5-dimethylpyridin-4-yl)-1-(tetrahydrofuran-3-yl)-1H-pyrazolo[4,3-c]quinolin-4(5H)-one (±)-7-(2-Methoxy-3,5-dimethylpyridin-4-yl)-1-(tetrahydrofuran-3-yl)-1H-pyrazolo[4,3-c]quinolin-4(5H)-one was analyzed by a chiral column chromatography [chiral column made by DAICEL Corp., AD-H (0.46 cm Φ×15 cm), mobile phrase; 100% ethanol] to identify (+)-form at 7.8 min and (−)-form at 9.7 min and confirm that optical resolution is possible. (±)-7-(2-Methoxy-3,5-dimethylpyridin-4-yl)-1-(tetrahydrofuran-3-yl)-1H-pyrazolo[4,3-c]quinolin-4(5H)-one (78 mg) was dissolved in a mixed solvent of ethanol (12 mL) and methanol (12 mL), and the solution was filtered through a cotton plug. The filtrate was optically resolved by chiral column chromatography [chiral column: AD-H column, elution solvent: 100% ethanol, flow rate: 10 mL/min, elution time: 80 minutes/elution, injection: 2 mL/injection, short retention time: (+)-form, long retention time: (−)-form] to give 26.4 mg of a (+)-form and 25.2 mg of a (−)-form of the title compound. $^1$H-NMR (400 MHz, CDCl$_3$) δ (ppm): 1.92-1.94 (m, 3H), 1.94-1.96 (m, 3H), 2.55-2.66 (m, 1H), 2.76-2.86 (m, 1H), 4.00 (s, 3H), 4.09-4.16 (m, 1H), 424-4.37 (m, 2H), 4.39-4.45 (m, 1H), 5.61-5.68 (m, 1H), 7.04 (d, J=1.5 Hz, 1H), 7.08 (dd, J=1.5 Hz, 8.3 Hz, 1H), 7.94 (s, 1H), 8.13 (d, J=8.3 Hz, 1H), 8.31 (s, 1H), 8.86 (s, 1H).

ESI-MS m/z 391 [M+H]$^+$ (S)-7-(2-methoxy-3,5-dimethylpyridin-4-yl)-1-(tetrahydrofuran-3-yl)-1H-pyrazolo[4,3-c]quinolin-4(5H)-one, synthesized according to the above-described Reference Example 1, was used in synthesis of the following salts.

Example 1

Synthesis of (S)-7-(2-methoxy-3,5-dimethylpyridin-4-yl)-1-(tetrahydrofuran-3-yl)-1H-pyrazolo[4,3-c]quinolin-4(5H)-one Monomaleate Salt To (S)-7-(2-methoxy-3,5-dimethylpyridin-4-yl)-1-(tetrahydrofuran-3-yl)-1H-pyrazolo[4,3-c]quinolin-4(5H)-one (576.32 mg) was added maleic acid (243.97 mg) and t-butyl methyl ether (6 mL), and the suspension was stirred at room temperature for 2 days. The solid was collected by filtration and dried under reduced pressure at room temperature, thereby giving the title compound (713.04 mg) as a white solid.

$^1$H-NMR (600 MHz, DMSO-d$_6$) δ (ppm): 1.87 (s, 3H), 1.91 (s, 3H), 2.52-2.56 (m, 2H), 3.89 (s, 3H), 3.93 (ddd, J=8, 7, 6 Hz, 1H), 4.03 (dddd, J=8, 8, 7, 2 Hz, 1H), 4.16 (ddd, J=9, 5, 3 Hz, 1H), 4.21 (dd, J=9, 6 Hz, 1H), 5.85-5.89 (m, 1H), 6.25 (s, 2H), 7.09 (dd, J=8, 1 Hz, 1H), 7.21 (d, J=1 Hz, 1H), 7.96 (s, 1H), 8.18 (s, 1H), 8.35 (d, J=8 Hz, 1H), 11.51 (s, 1H).

$^{13}$C-NMR (100 MHz, solid state) δ (ppm): 13.3, 16.1, 16.7, 29.5, 35.9, 57.2, 58.0, 61.9, 67.4, 69.7, 74.6, 111.8, 114.3, 122.5, 123.2, 125.7, 126.9, 127.9, 132.7, 133.8, 136.0, 138.9, 154.8, 156.2, 157.8, 158.9, 162.0, 163.4, 164.7, 172.0

Powder X-ray diffraction angles (2θ±0.2°): 9.1°, 10.1°, 11.1°, 16.2°, 17.6°, 18.2°, 22.0°, 22.4°, 23.8°, 25.8°.

The powder X-ray diffraction pattern of the crystal of the (S)-7-(2-methoxy-3,5-dimethylpyridin-4-yl)-1-(tetrahydrofuran-3-yl)-1H-pyrazolo[4,3-c]quinolin-4(5H)-one monomaleate salt, obtained by the above-described method, is shown in FIG. 1.

Example 2

Synthesis of (S)-7-(2-methoxy-3,5-dimethylpyridin-4-yl)-1-(tetrahydrofuran-3-yl)-1H-pyrazolo[4,3-c]quinolin-4(5H)-one Monobenzenesulfonate Salt To (S)-7-(2-methoxy-3,5-dimethylpyridin-4-yl)-1-(tetrahydrofuran-3-yl)-1H-pyrazolo[4,3-c]quinolin-4(5H)-one (991.7 mg) was added 2-butanone (10 mL) and benzenesulfonic acid monohydrate (708.0 mg), and the suspension was stirred at room temperature for 2 days. The solid material was collected by filtration and dried under reduced pressure at room temperature, thereby giving the title compound (1393.9 mg) as a white solid.

$^1$H-NMR (600 MHz, DMSO-d$_6$) δ (ppm): 1.87 (s, 3H), 1.91 (s, 3H), 2.52-2.56 (m, 2H), 3.89 (s, 3H), 3.93 (ddd, J=8, 7, 6 Hz, 1H), 4.01-4.05 (m, 1H), 4.16 (ddd, J=9, 5, 3 Hz, 1H), 4.21 (dd, J=9, 6 Hz, 1H), 5.85-5.89 (m, 1H), 7.09 (dd, J=8, 1 Hz, 1H), 7.22 (d, J=1 Hz, 1H), 7.32-7.26 (m, 3H), 7.59-7.57 (m, 2H), 7.96 (s, 1H), 8.18 (s, 1H), 8.35 (d, J=8 Hz, 1H), 11.51 (s, 1H).

$^{13}$C-NMR (100 MHz, solid state) δ (ppm): 12.8, 16.8, 31.3, 35.2, 59.1, 61.0, 61.6, 62.0, 67.9, 70.1, 70.6, 74.7, 111.6, 114.0, 117.5, 122.7, 125.4, 126.8, 128.8, 130.1, 137.7, 139.2, 146.4, 157.8, 159.6, 160.7

Powder X-ray diffraction angles (2θ±0.2°): 6.6°, 9.9°, 13.7°, 14.6°, 19.0°, 19.6°, 20.5°, 21.7°, 22.7°, 23.5°, 25.7°.

Figure 2:
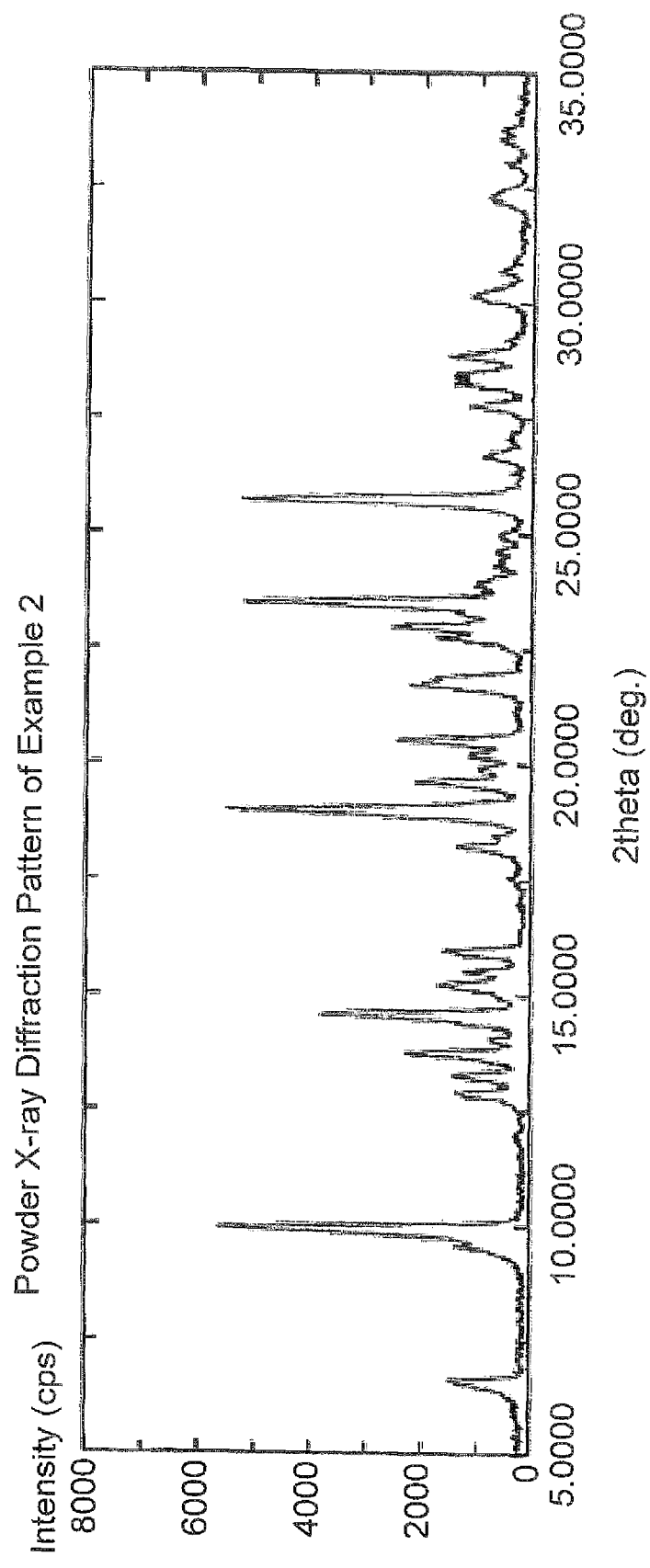
FIG. 2 is a powder X-ray diffraction pattern of the crystal of the compound (I) monobenzenesulfonate salt obtained in Example 2. The abscissa shows the diffraction angle (2θ) and the ordinate shows the peak intensity.

The powder X-ray diffraction pattern of the crystal of the (S)-7-(2-methoxy-3,5-dimethylpyridin-4-yl)-1-(tetrahydrofuran-3-yl)-1H-pyrazolo[4,3-c]quinolin-4(5H)-one monobenzenesulfonate salt, obtained by the above-described method, is shown in FIG. 2.

Example 3

Synthesis of (S)-7-(2-methoxy-3,5-dimethylpyridin-4-yl)-1-(tetrahydrofuran-3-yl)-1H-pyrazolo[4,3-c]quinolin-4(5H)-one Hydrochloride Salt To (S)-7-(2-methoxy-3,5-dimethylpyridin-4-yl)-1-(tetrahydrofuran-3-yl)-1H-pyrazolo[4,3-c]quinolin-4(5H)-one (984.6 mg) was added acetone (20 mL) and 5N hydrochloric acid (620 μL), and the suspension was stirred at room temperature for 2 days. The solid material was collected by filtration and dried under reduced pressure at room temperature, thereby giving the title compound (1100.21 mg) as a white solid.

Powder X-ray diffraction angles (2θ±0.2°): 11.2°, 12.4°, 12.7°, 17.1°, 23.5°, 26.5°, 29.4°.

Figure 3:
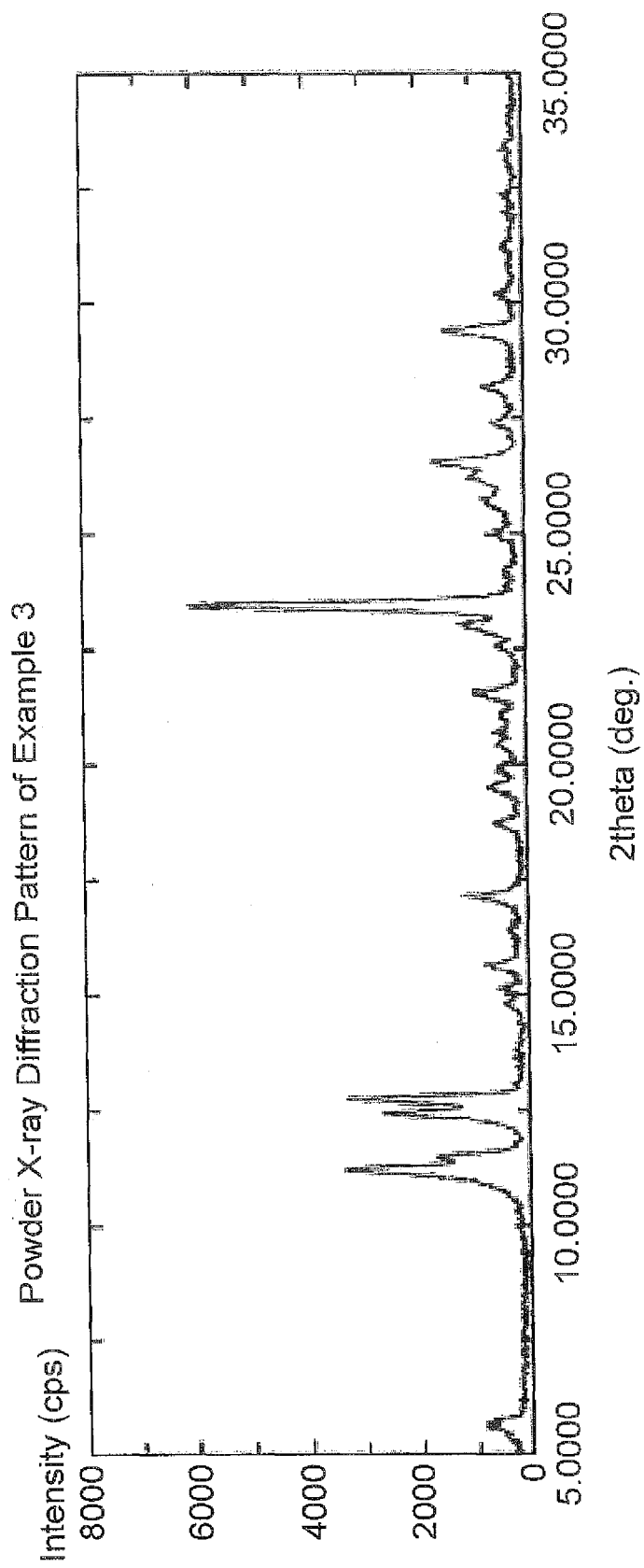
FIG. 3 is a powder X-ray diffraction pattern of the crystal of the compound (I) hydrochloride salt obtained in Example 3. The abscissa shows the diffraction angle (2θ) and the ordinate shows the peak intensity.

The powder X-ray diffraction pattern of the crystal of the (S)-7-(2-methoxy-3,5-dimethylpyridin-4-yl)-1-(tetrahydrofuran-3-yl)-1H-pyrazolo[4,3-c]quinolin-4(5H)-one hydrochloride salt, obtained by the above-described method, is shown in FIG. 3.

Example 4

Synthesis of (S)-7-(2-methoxy-3,5-dimethylpyridin-4-yl)-1-(tetrahydrofuran-3-yl)-1H-pyrazolo[4,3-c]quinolin-4(5H)-one Hydrobromide Salt To (S)-7-(2-methoxy-3,5-dimethylpyridin-4-yl)-1-(tetrahydrofuran-3-yl)-1H-pyrazolo[4,3-c]quinolin-4(5H)-one (614.45 mg) was added acetone (6 mL) and 47% hydrobromic acid (220 μL), and the suspension was stirred at room temperature overnight.

The solid material was collected by filtration and dried under reduced pressure at room temperature, thereby giving the title compound (719.23 mg) as a white solid.

Powder X-ray diffraction angles (2θ±0.2°): 5.6°, 11.1°, 12.3°, 18.5°, 19.3°, 22.9°, 23.4°, 26.3°, 29.2°.

Figure 4:
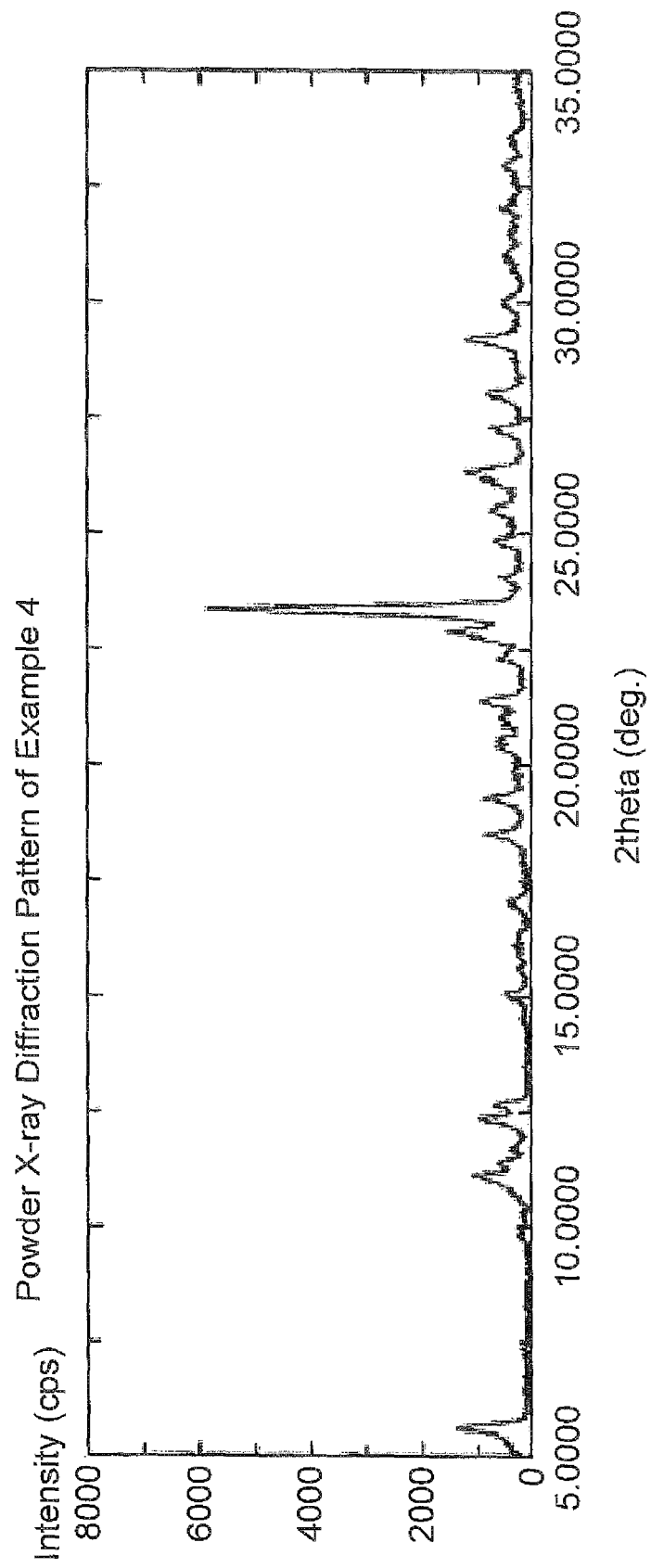
FIG. 4 is a powder X-ray diffraction pattern of the crystal of the compound (I) hydrobromide salt obtained in Example 4. The abscissa shows the diffraction angle (2θ) and the ordinate shows the peak intensity.

The powder X-ray diffraction pattern of the crystal of the (S)-7-(2-methoxy-3,5-dimethylpyridin-4-yl)-1-(tetrahydrofuran-3-yl)-1H-pyrazolo[4,3-c]quinolin-4(5H)-one hydrobromide salt, obtained by the above-described method, is shown in FIG. 4.

Example 5

Synthesis of (S)-7-(2-methoxy-3,5-dimethylpyridin-4-yl)-1-(tetrahydrofuran-3-yl)-1H-pyrazolo[4,3-c]quinolin-4(5H)-one p-Toluenesulfonate Salt To (S)-7-(2-methoxy-3,5-dimethylpyridin-4-yl)-1-(tetrahydrofuran-3-yl)-1H-pyrazolo[4,3-c]quinolin-4(5H)-one (100.6 mg) was added 2-butanone (4 mL) and p-toluenesulfonic acid (65.1 mg), and the suspension was stirred at room temperature overnight. The solid material was collected by filtration and dried under reduced pressure at room temperature, thereby giving the title compound (153.15 mg) as a white solid.

Powder X-ray diffraction angles (2θ±0.2°): 6.5°, 9.8°, 13.9°, 14.4°, 15.3°, 18.5°, 19.3°, 20.3°, 22.8°, 23.3°, 25.4°, 28.2°.

Figure 5:
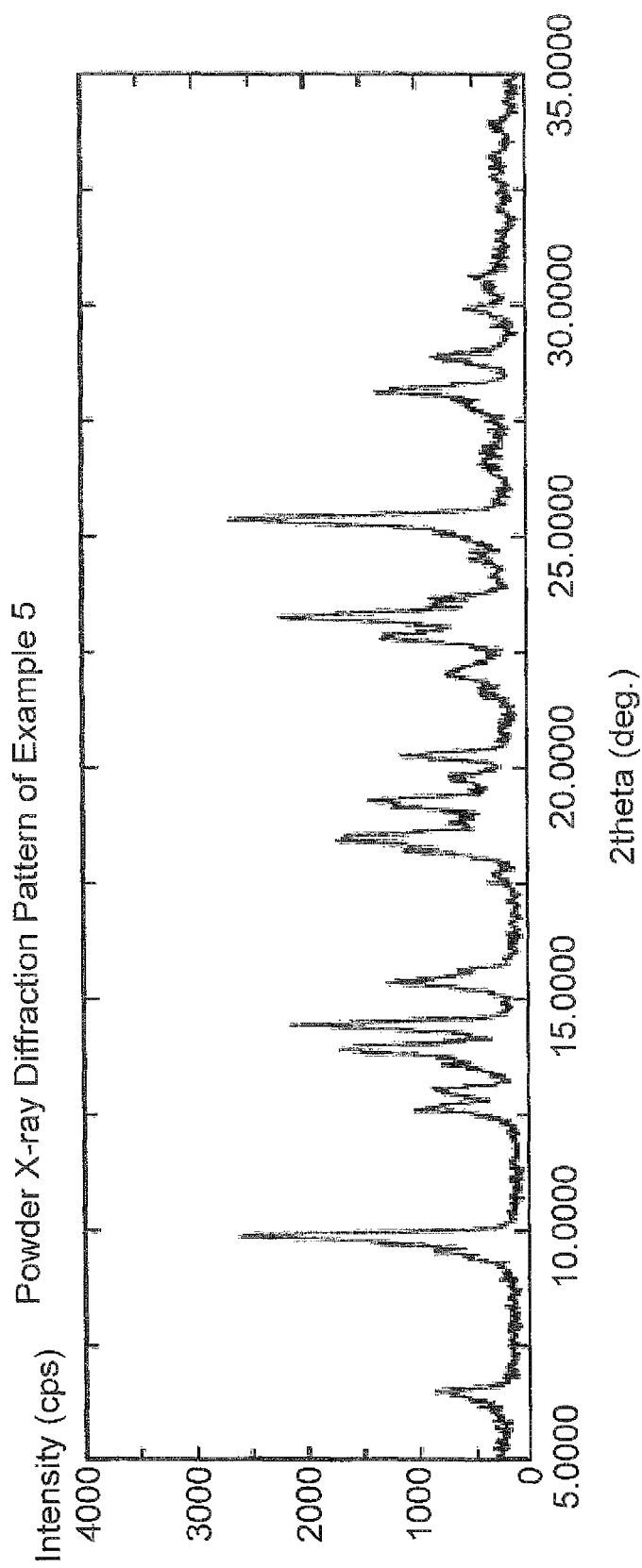
FIG. 5 is a powder X-ray diffraction pattern of the crystal of the compound (I) p-toluenesulfonate salt obtained in Example 5. The abscissa shows the diffraction angle (2θ) and the ordinate shows the peak intensity.

The powder X-ray diffraction pattern of the crystal of the (S)-7-(2-methoxy-3,5-dimethylpyridin-4-yl)-1-(tetrahydrofuran-3-yl)-1H-pyrazolo[4,3-c]quinolin-4(5H)-one p-toluenesulfonate salt, obtained by the above-described method, is shown in FIG. 5.

Example 6

Synthesis of (S)-7-(2-methoxy-3,5-dimethylpyridin-4-yl)-1-(tetrahydrofuran-3-yl)-1H-pyrrolo[4,3-c]quinolin-4(5H)-one Nitrate Salt To (S)-7-(2-methoxy-3,5-dimethylpyridin-4-yl)-1-(tetrahydrofuran-3-yl)-1H-pyrazolo[4,3-c]quinolin-4(5H)-one (22.80 mg) was added ethyl acetate (300 μL) and 60% nitric acid (5.3 μL), and the suspension was stirred at room temperature overnight. The solid material was collected by filtration and dried under reduced pressure at room temperature, thereby giving the title compound (14.97 mg) as a white solid.

Powder X-ray diffraction angles (2θ±0.2°): 11.1°, 11.7°, 14.8°, 15.3°, 16.4°, 19.2°, 23.6°, 24.2°, 25.8°.

Figure 6:
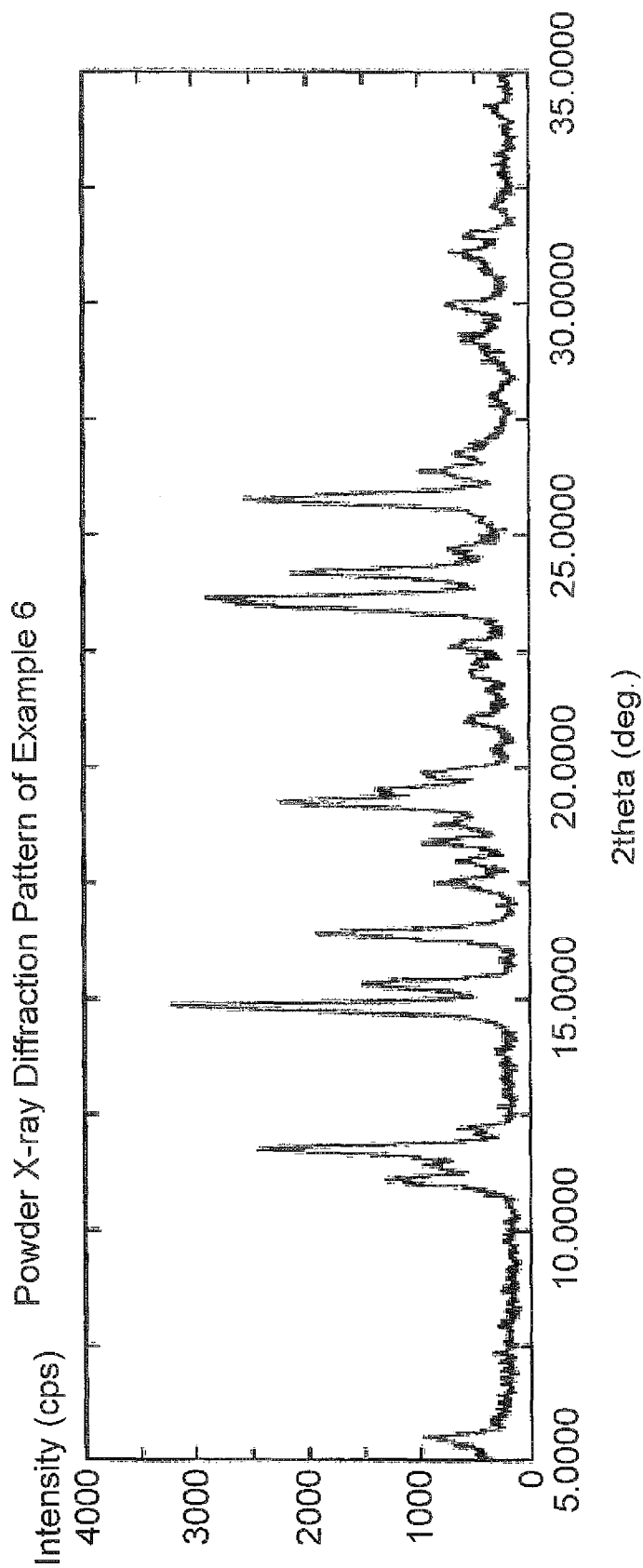
FIG. 6 is a powder X-ray diffraction pattern of the crystal of the compound (I) nitrate salt obtained in Example 6. The abscissa shows the diffraction angle (2θ) and the ordinate the peak intensity.

The powder X-ray diffraction pattern of the crystal of the (S)-7-(2-methoxy-3,5-dimethylpyridin-4-yl)-1-(tetrahydrofuran-3-yl)-1H-pyrazolo[4,3-c]quinolin-4(5H)-one nitrate salt, obtained by the above-described method, is shown in FIG. 6.

Example 7

Synthesis of (S)-7-(2-methoxy-3,5-dimethylpyridin-4-yl)-1-(tetrahydrofuran-3-yl)-1H-pyrazolo[4,3-c]quinolin-4(5H)-one Sulfate Salt To (S)-7-(2-methoxy-3,5-dimethylpyridin-4-yl)-1-(tetrahydrofuran-3-yl)-1H-pyrazolo[4,3-c]quinolin-4(5H)-one (23.53 mg) was added 2-butanone (300 μL) and 95% sulfuric acid (4 μL), and the suspension was stirred at room temperature overnight. The solid material was collected by filtration and dried under reduced pressure at room temperature, thereby giving the title compound (27.34 mg) as a white solid.

Powder X-ray diffraction angles (2θ±0.2°): 10.7°, 14.0°, 14.5°, 16.2°, 19.1°, 20.0°, 22.8°, 23.6°, 25.3°.

Figure 7:
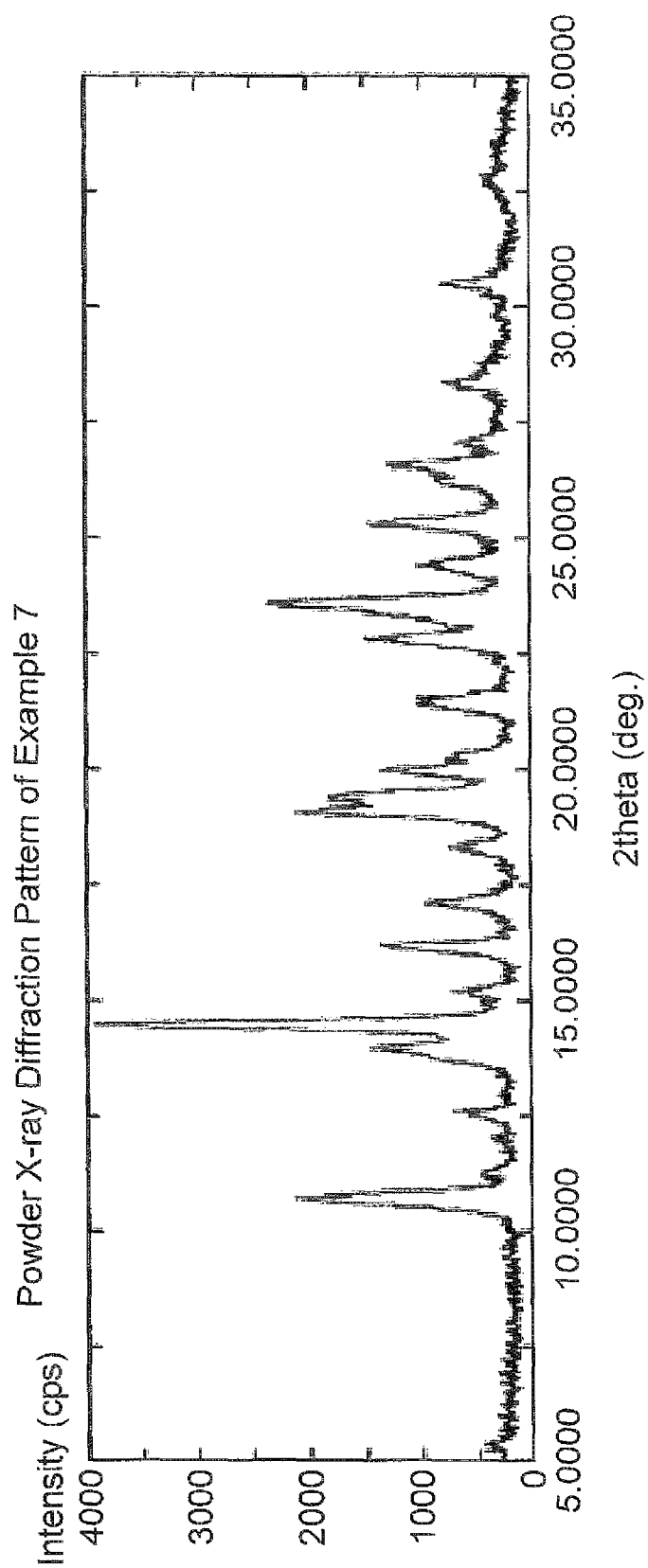
FIG. 7 is a powder X-ray diffraction pattern of the crystal of the compound (I) sulfate salt obtained in Example 7. The abscissa shows the diffraction angle (2θ) and the ordinate shows the peak intensity.

The powder X-ray diffraction pattern of the crystal of the (S)-7-(2-methoxy-3,5-dimethylpyridin-4-yl)-1-(tetrahydrofuran-3-yl)-1H-pyrazolo[4,3-c]quinolin-4(5H)-one sulfate salt, obtained by the above-described method, is shown in FIG. 7.

Example 8

Synthesis of (S)-7-(2-methoxy-3,5-dimethylpyridin-4-yl)-1-(tetrahydrofuran-3-yl)-1H-pyrazolo[4,3-c]quinolin-4(5)-one Methanesulfonate Salt To (S)-7-(2-methoxy-3,5-dimethylpyridin-4-yl)-1-(tetrahydrofuran-3-yl)-1H-pyrazolo[4,3-c]quinolin-4(5H)-one (22.52 mg) was added 2-butanone (300 μL) and methanesulfonic acid (4.5 μL), and the suspension was stirred at room temperature overnight. The solid material was collected by filtration and dried under reduced pressure at room temperature, thereby giving the title compound (28.69 mg) as a white solid.

Powder X-ray diffraction angles (2θ±0.2°): 12.7°, 14.8°, 17.8°, 18.7°, 23.4°, 29.8°.

Figure 8:
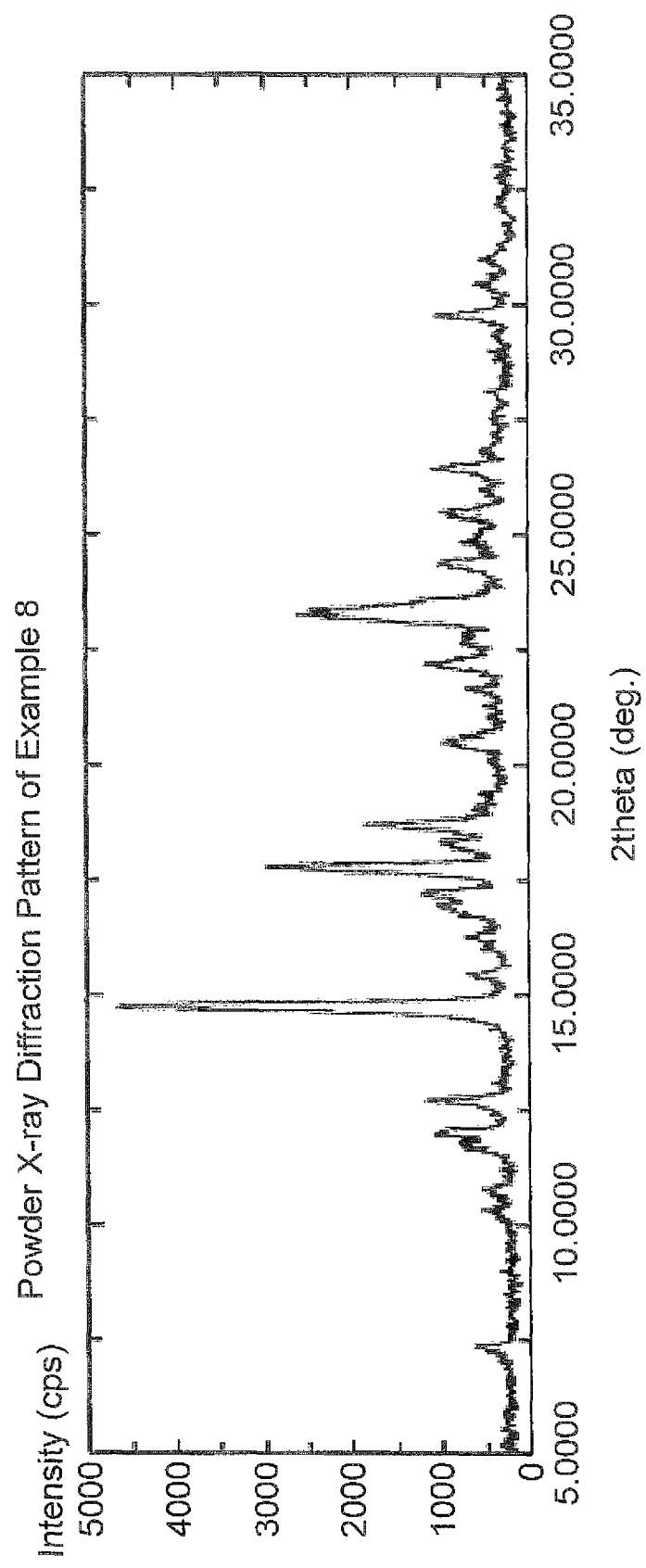
FIG. 8 is a powder X-ray diffraction pattern of the crystal of the compound (I) methanesulfonate salt obtained in Example 8. The abscissa shows the diffraction angle (2θ) and the ordinate shows the peak intensity.

The powder X-ray diffraction pattern of the crystal of the (S)-7-(2-methoxy-3,5-dimethylpyridin-4-yl)-1-(tetrahydrofuran-3-yl)-1H-pyrazolo[4,3-c]quinolin-4(5H)-one methanesulfonate salt, obtained by the above-described method, is shown in FIG. 8.

Example 9

Synthesis of (S)-7-(2-methoxy-3,5-dimethylpyridin-4-yl)-1-(tetrahydrofuran-3-yl)-1H-pyrazolo[4,3-c]quinolin-4(5H)-one Phosphate Salt To (S)-7-(2-methoxy-3,5-dimethylpyridin-4-yl)-1-(tetrahydrofuran-3-yl)-1H-pyrazolo[4,3-c]quinolin-4(5H)-one (22.29 mg) was added 2-butanone (300 μL) and phosphoric acid (4.6 μL), and the suspension was stirred at room temperature overnight. After further addition of hexane (200 μL) and stirring, the solid material was collected by filtration and dried under reduced pressure at room temperature, thereby giving the title compound (23.09 mg) as a white solid.

Powder X-ray diffraction angles (2θ±0.2°): 9.5°, 11.3°, 15.2°, 16.7°, 18.4°, 23.5°, 24.0°.

Figure 9:
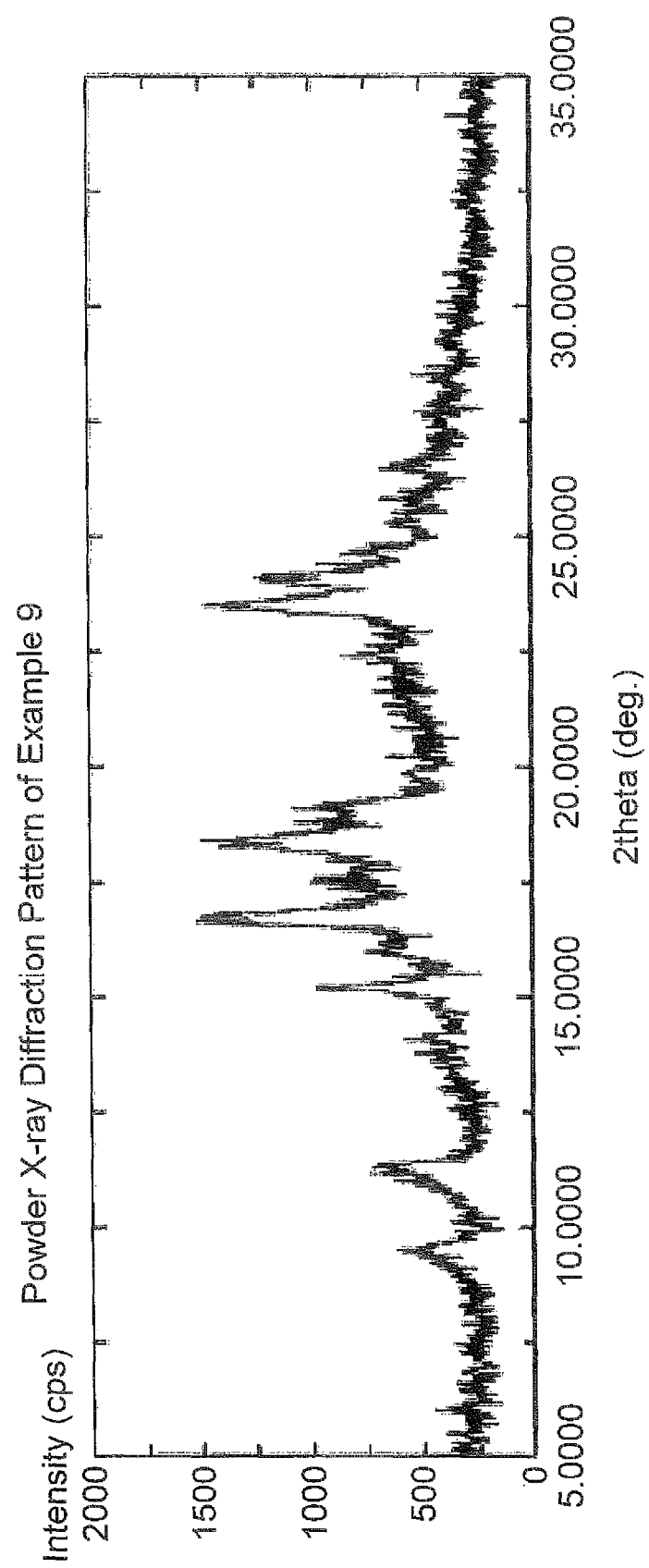
FIG. 9 is a powder X-ray diffraction pattern of the crystal of the compound (I) phosphate salt obtained in Example 9. The abscissa shows the diffraction angle (2θ) and the ordinate shows the peak intensity.

The powder X-ray diffraction pattern of the crystal of the (S)-7-(2-methoxy-3,5-dimethylpyridin-4-yl)-1-(tetrahydrofuran-3-yl)-1H-pyrazolo[4,3-c]quinolin-4(5H)-one phosphate salt, obtained by the above-described method, is shown in FIG. 9.

Example 10

Synthesis of (S)-7-(2-methoxy-3,5-dimethylpyridin-4-yl)-1-(tetrahydrofuran-3-yl)-1H-pyrazolo[4,3-c]quinolin-4(5H)-one L-tartrate Salt To (S)-7-(2-methoxy-3,5-dimethylpyridin-4-yl)-1-(tetrahydrofuran-3-yl)-1H-pyrazolo[4,3-c]quinolin-4(5H)-one (27.42 mg) was added acetone (300 μL) and L-tartaric acid (20.18 mg), and the suspension was stirred at room temperature for 3 days. The solid material was collected by filtration and dried under reduced pressure at room temperature, thereby giving the title compound (34.89 mg) as a white solid.

Powder X-ray diffraction angles (2θ±0.2°): 10.1°, 14.1°, 16.7°, 17.4°, 18.2°, 20.6°, 23.4°, 24.0°, 24.3°, 26.5°.

Figure 10:
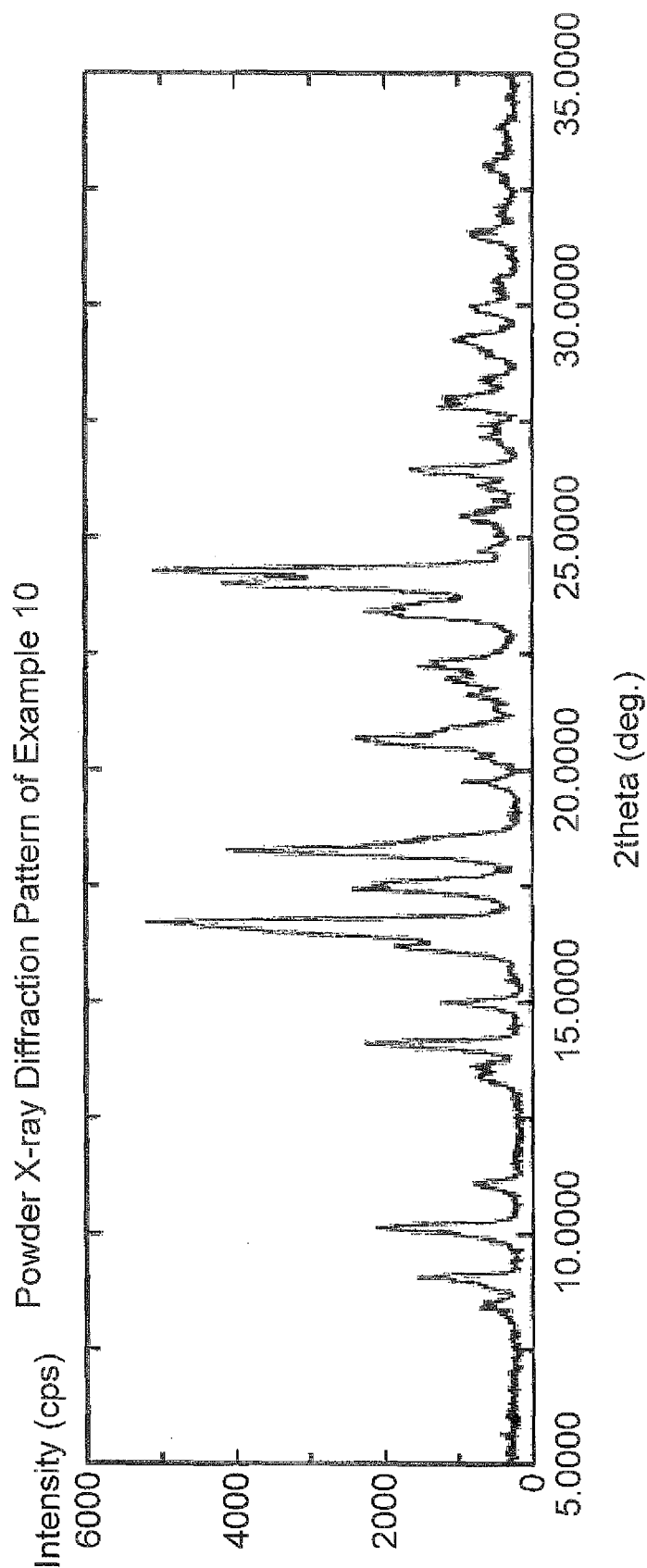
FIG. 10 is a powder X-ray diffraction pattern of the crystal of the compound (I) L-tartrate salt obtained in Example 10. The abscissa shows the diffraction angle (2θ) and the ordinate shows the peak intensity.

The powder X-ray diffraction pattern of the crystal of the (S)-7-(2-methoxy-3,5-dimethylpyridin-4-yl)-1-(tetrahydrofuran-3-yl)-1H-pyrazolo[4,3-c]quinolin-4(5H)-one L-tartrate salt, obtained by the above-described method, is shown in FIG. 10.

Example 11

Synthesis of (S)-7-(2-methoxy-3,5-dimethylpyridin-4-yl)-1-(tetrahydrofuran-3-yl)-1H-pyrazolo[4,3-c]quinolin-4(5H)-one Malonate Salt To (S)-7-(2-methoxy-3,5-dimethylpyridin-4-yl)-1-(tetrahydrofuran-3-yl)-1H-pyrazolo[4,3-c]quinolin-4(5H)-one (27.70 mg) was added acetone (300 μL) and malonic acid (26.65 mg), and the suspension was stirred at room temperature for 3 days. The solid material was collected by filtration and dried under reduced pressure at room temperature, thereby giving the title compound (30.49 mg) as a white solid.

Powder X-ray diffraction angles (2θ±0.2°): 10.5°, 16.8°, 17.4°, 17.8°, 18.3°, 18.9°, 21.7°, 22.8°, 24.2°, 25.2°, 26.4°.

Figure 11:
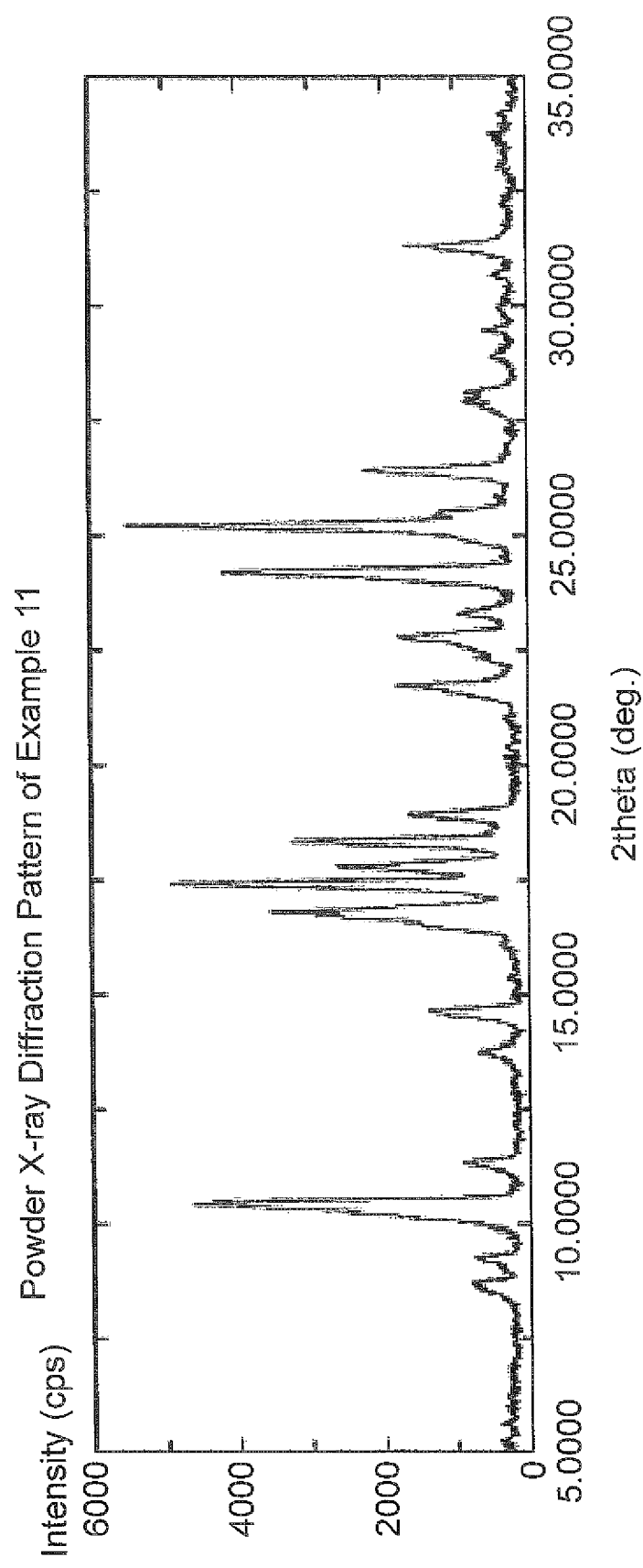
FIG. 11 is a powder X-ray diffraction pattern of the crystal of the compound (I) malonate salt obtained in Example 11. The abscissa shows the diffraction angle (2θ) and the ordinate shows the peak intensity.

The powder X-ray diffraction pattern of the crystal of the (S)-7-(2-methoxy-3,5-dimethylpyridin-4-yl)-1-(tetrahydrofuran-3-yl)-1H-pyrazolo[4,3-c]quinolin-4(5H)-one malonate salt, obtained by the above-described method, is shown in FIG. 11.

Example 12

Synthesis of (S)-7-(2-methoxy-3,5-dimethylpyridin-4-yl)-1-(tetrahydrofuran-3-yl)-1H-pyrazolo[4,3-c]quinolin-4(5H)-one Monomaleate Salt To (S)-7-(2-methoxy-3,5-dimethylpyridin-4-yl)-1-(tetrahydrofuran-3-yl)-1H-pyrazolo[4,3-c]quinolin-4(5H)-one (500 mg) was added ethyl acetate (2 mL), and the mixture was stirred at 25° C. for 20 minutes. A solution of maleic acid (223.0 mg) completely dissolved in ethyl acetate (7.5 mL) was added to the above suspension, and the mixture was stirred at 25° C. for 7 days. The solid was collected by filtration, and the crystal was washed with ethyl acetate (1 mL) and dried under reduced pressure at 40° C., thereby giving the title compound (366.9 mg) as a white solid.

The obtained title compound showed the same powder X-ray diffraction peaks as Example 1.

Test Examples

A PDE9 Inhibitory Activity Test Example

1) Preparation of a Human Recombinant PDE9 Protein

An hsPDE9A 1cDNA fragment was amplified by being based on a base sequence (Accession No.: AF048837) of the hsPDE9A1 registered on GenBank data base, and by using the following sequences (Hokkaido System Science Co., Ltd.) as a primer and Human hippocampus cDNA library (Clontech Laboratories, Inc.) as a template DNA, and using Pfu50 DNA polymerase (Invitrogen Corp.), and by a polymerase chain reaction (PCR) of the following condition.

```
An hPDE9-1 primer:
                                    (SEQ No. 1)
AGGATGGGATCCGGCTCCTCCA An hPDE9A-3 primer:
                                    (SEQ No. 2)
CAGGCACAGTCTCCTTCACTG
```

The condition of PCR: [96° C., 5 min]×1 cycle, [(96° C., 10 sec), (57° C., 5 sec), (72° C., 2 min)]×30 cycles The obtained hsPDE9A 1cDNA fragment was incorporated in a TOPO-TA cloning vector (Invitrogen Corp.), and the base sequence was checked; and thereafter, the resultant was transfected in a pcDNA 3.1/myc His-tag vector (Invitrogen Corp.) to thereby make a human PDE9 expression vector for mammal cells. The human PDE9 expression vector for mammal cells was transfected with transient expression to an HEK293 cell by using a LIPOFETAMINE 2000 Reagent (Gibco). It was confirmed by Western blot method that the PDE9A expressed in the HEK293 cell, and then, the human PDE9A 1cDNA fragment was transfected in a pYNG vector (Katakura Industries Co., Ltd.) to thereby make an expression vector for insect cells. A supernatant of homogenized silk worm in which a large amount of PDE9 was expressed was purified by an equilibrated Ni column using a buffer A (20 mmol/L Tris-HCl, pH: 8.0, 1 mmol/L DTT, 10 mmol/L imidazole). After 1 hour of mixing of the supernatant and the Ni column, cleaning was carried out using a buffer B (20 mmol/L Tris-HCl, pH: 8.0, 1 mmol/L DTT), and elution was carried out using a buffer C (20 mmol/L Tris-HCl, pH: 8.0, 1 mmol/L DTT, 100 mmol/L imidazole). An elution fraction was preparatively collected to thereby obtain a PDE9 enzyme solution.

2) Measurement of PDE9 Inhibitory Action

To 100 µL of a buffer D (40 mmol/L Tris-HCl, pH: 7.4, 10 mmol/L $MgCl_2$, 1 mM DTT, 2 µM cGMP) solution containing [$^3$H]-cGMP (0.5 µCi/mL), 10 µL of a compound solution for evaluation (a solution in which a compound was dissolved in DMSO and diluted so that the DMSO concentration became 5%) and 90 µL of a solution prepared by diluting the PDE9 enzyme solution prepared in the above with a buffer E (40 mmol/L Tris-HCl, pH: 7.4, 10 mmol/L $MgCl_2$, 1 mM DTT, 1 mmol/L EGTA) were added under ice cooling. The resultant mixed solution was incubated at 30° C. for 10 min, and thereafter heated for 2 min in boiled water to stop the enzyme reaction of the PDE9. Then, the resultant was returned to room temperature; 50 µL of 5'-Nucleotidase (Biomol GmbH, 10 units/mL) was added thereto; and the resultant was incubated at 30° C. for 10 min to thereby convert [$^3$H]-5'-GMP formed in the previous reaction to [$^3$H]-guanosine. 500 µL of an anion exchange resin (Bio-Rad AG1-X2 resin, mesh size: 200-400, $H_2O$:resin=2:1) was added to the resultant reaction liquid, and allowed to stand for 10 min, and thereafter centrifuged (2,000 rpm, 10 min); and a supernatant in which the [$^3$H]-guanosine was present was transferred to a LumaPlate (PerkinElmer, Inc.), and the radioactivity was measured by a TopCount NXT microplate scintillation and luminescence counter (PerkinElmer, Inc.).

The inhibition percentage of the evaluation compound was calculated using the following expression, taking the radioactivity of a control containing no evaluation compound to be (A), the radioactivity of a blank containing no enzyme to be (B), and the radioactivity of the evaluation compound to be (C).

$$\text{Inhibition percentage} = 100 - \{[(C)-(B)]/[(A)-(B)]\} \times 100(\%)$$

The $IC_{50}$ value for PDE9 of the evaluation compound was determined from inhibition percentage for various concentrations. The $IC_{50}$ value of the compound (I) synthesized according to Reference Example 2 against PDE9 was 0.00943 µM.

Effect on Rodent Cerebrospinal Fluid cGMP

Test compounds were administered to ICR male mice (CHARLES RIVER LABORATORIES JAPAN, INC.), Sprague-Dawley (SD) male rats (CHARLES RIVER LABORATORIES JAPAN, INC.) or Long-Evans (LE) male rats (Institute for Animal Reproduction (general incorporated foundation)), and then cerebrospinal fluid was collected under pentobarbital anesthesia and stored at −20° C. Measurement of cGMP in cerebrospinal fluid was performed according to the acetylation EIA procedure of cGMP EIA kit (GE Healthcare) or the non-acetylation procedure of cGMP EIA kit (Cayman Chemical). The results were calculated using the following formula as an increase (C) in the amount of cGMP in the test compound-administered group (B) relative to the amount of cGMP in the vehicle-administered group (A).

$$\text{cGMP increase}(C)=[(B)-(A)]/(A)\times100(\%)$$

In the case of the compound (I) synthesized according to Reference Example 1, the cGMP increase was 274% at 1 hour post-administration of a dose of 10 mg/kg to LE rats.

Effect on Rodent Hippocampal cGMP

Test compounds were administered to SD male rats (CHARLES RIVER LABORATORIES JAPAN, INC.) or LE male rats (Institute for Animal Reproduction (foundation)). Then a microwave treatment was performed under pentobarbital anesthesia, and the hippocampus were isolated, subjected to measurement of their wet weights, then frozen in liquid nitrogen and stored at −80° C. In the measurement of cGMP in the hippocampus, a 0.5 M perchloric acid/1 mM EDTA solution was added so that the wet weight would constitute 5% (w/v), and the mixture was homogenized. After the homogenization, the homogenate was centrifuged (10000 rpm, 15 min), and the supernatant was collected. The collected supernatant was neutralized with a 2 M potassium hydrogen carbonate solution and centrifuged (13000 rpm, 10 min) The cGMP concentration in the supernatant was measured according to the non-acetylation EIA procedure of cGMP EIA kit (GE Healthcare). The results were calculated using the following formula as an increase (C) in the amount of cGMP in the test compound-administered group (B) relative to the amount of cGMP in the vehicle-administered group (A).

cGMP increase($C$)=[($B$)−($A$)]/($A$)×100(%)

In the case of the compound (I) synthesized according to Reference Example 1, the cGMP increase was 58% at 1 hour post-administration of a dose of 10 mg/kg to LE rats.

Dissolution Test

Figure 12:
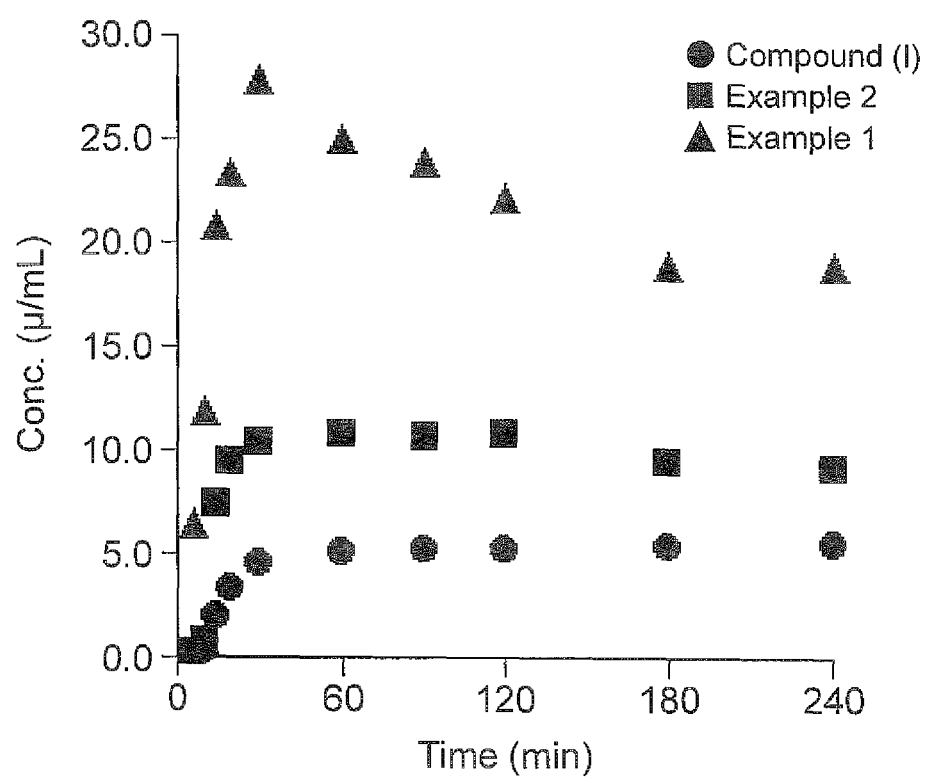
FIG. 12 is a graph showing the results of the dissolution test performed on compound (I), the compound (I) monomaleate salt obtained in Example 1 and the compound (I) monobenzenesulfonate salt obtained in Example 2. The abscissa shows time (minutes) and the ordinate shows the concentration (μg/mL) in terms of compound (I).

Each of compound (I) (50 mg), the compound of Example 1 (30 mg) and the compound of Example 2 (30 mg) was filled into a hydroxypropyl methylcellulose capsule, together with an equal weight of lactose hydrate. A 708-DS from Agilent Technologies was equipped with small stirring paddles and small vessels, and used as a dissolution test apparatus. Each drug-filled capsule was added to 50 ml of fasted state simulated intestinal fluid (a phosphate buffer pH 6.5 containing 0.75 mM lecithin and 3 mM sodium taurocholate) which had been warmed to 37° C. The drug was dissolved by rotating the stirring paddle at a speed of 50 rpm. The dissolved solution was sampled over time and the drug concentrations were measured by HPLC. Such dissolution tests using fasted state simulated intestinal fluid are often used to evaluate the dissolution and absorption characteristics of drugs (e.g., Takano et al., "Oral absorption of poorly water-soluble drugs: computer simulation of fraction absorbed in humans from a miniscale dissolution test", Pharm Res., vol. 23, pp. 1144-1156, 2006). The results were shown in Table 1 and the graph in FIG. 12. The concentration of the compound of Example 2 achieved when using it showed about 2-fold higher values and the concentration of the compound of Example 1 achieved when using it about 4- to 5-fold higher values, relative to the concentration of compound (I) achieved when using it.

TABLE 1

| TIME | CONCENTRATION (μg/mL) | | |
|---|---|---|---|
| (MINUTES) | COMPOUND (I) | EXAMPLE 1 | EXAMPLE 2 |
| 6 | 0.1 | 6.4 | 0.0 |
| 10 | 0.3 | 11.8 | 0.5 |
| 15 | 1.8 | 20.8 | 7.3 |
| 20 | 3.2 | 23.3 | 9.3 |
| 30 | 4.4 | 27.9 | 10.2 |
| 60 | 5.0 | 25.0 | 10.7 |
| 90 | 5.2 | 23.9 | 10.6 |
| 120 | 5.1 | 22.1 | 10.7 |
| 180 | 5.2 | 18.8 | 9.4 |
| 240 | 5.4 | 18.8 | 9.0 |

Test on Oral Absorption Characteristics in Dogs

Figure 13:
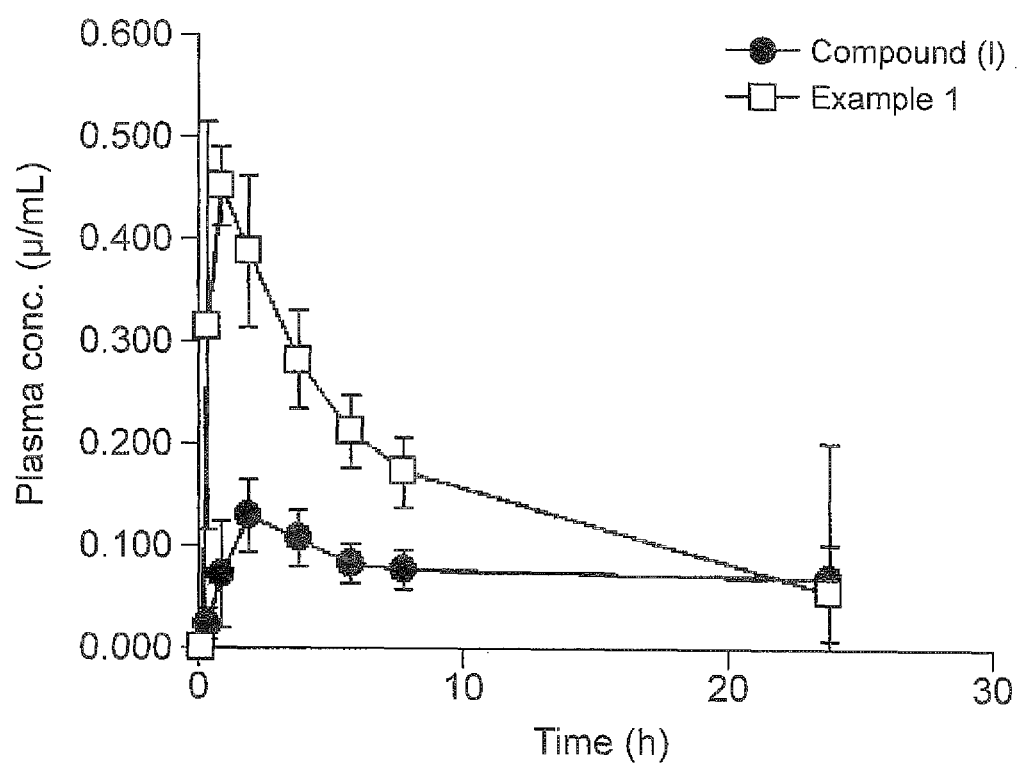
FIG. 13 is a graph showing changes in plasma concentration of compound (I) upon oral administration of compound (I) and the compound (I) monomaleate salt, obtained in Example 1, to dogs. The abscissa shows time (hours) and the ordinate shows the concentration of the compound (μg/mL) in terms of compound (I).

Each of compound (I) (100 mg) and the compound of Example 1 (130 mg the monomaleate salt, 100 mg in terms of the free form) was filled into a hydroxypropyl methylcellulose capsule to make a sample for administration. The resultant capsules were administered, together with a small amount of water, to 4 beagle dogs, and blood was collected at each time points of 0.5, 1, 2, 4, 6, 8 and 24 hours after administration. The drug concentration in the plasma obtained by centrifugation was measured by LC-MS/MS. Compound (I) and the compound of Example 1 were administered to each individual in a crossover fashion with one week of washout period in between, and changes in drug concentration in the plasma were compared. The results were shown in Table 2 and the graph in FIG. 13. BQL means below the quantification limit, and NC not calculated. The values for the area under the plasma drug concentration-time curve (AUC) are shown in Table 3. The mean AUC value obtained when administering compound (I) was 1.88±0.95 μg·h/mL while the mean AUC value obtained when administering the compound of Example 1 was 4.00±0.45 μg·h/mL: the absorption rate was higher and the variation in the values smaller with the compound of Example 1.

Thus, the salts/crystals according to the present invention showed preferable dissolution and oral absorption characteristics as raw materials for pharmaceuticals.

TABLE 2

| | PLASMA CONCENTRATION (μg/mL) | | | | | |
|---|---|---|---|---|---|---|
| TIME (HOURS) | Dog. 1 | Dog. 2 | Dog. 3 | Dog. 4 | MEAN | STANDARD DEVIATION |
| | COMPOUND (I) | | | | | |
| 0.25 | BQL | BQL | BQL | BQL | NC | NC |
| 0.5 | 0.005 | 0.029 | 0.034 | BQL | 0.023 | 0.015 |
| 1 | 0.055 | 0.067 | 0.142 | 0.017 | 0.070 | 0.052 |
| 2 | 0.094 | 0.061 | 0.133 | 0.227 | 0.129 | 0.036 |
| 4 | 0.064 | 0.051 | 0.104 | 0.208 | 0.106 | 0.028 |
| 6 | 0.045 | 0.045 | 0.077 | 0.164 | 0.083 | 0.019 |
| 8 | 0.043 | 0.041 | 0.074 | 0.151 | 0.077 | 0.019 |
| 24 | 0.234 | 0.007 | 0.009 | 0.028 | 0.069 | 0.130 |
| | EXAMPLE 1 | | | | | |
| 0.25 | BQL | BQL | 0.279 | BQL | NC | NC |
| 0.5 | 0.428 | 0.140 | 0.377 | 0.006 | 0.315 | 0.199 |
| 1 | 0.506 | 0.457 | 0.422 | 0.422 | 0.452 | 0.039 |
| 2 | 0.343 | 0.469 | 0.337 | 0.401 | 0.388 | 0.074 |
| 4 | 0.219 | 0.313 | 0.272 | 0.322 | 0.282 | 0.047 |
| 6 | 0.158 | 0.224 | 0.217 | 0.248 | 0.212 | 0.036 |
| 8 | 0.134 | 0.199 | 0.147 | 0.210 | 0.172 | 0.035 |
| 24 | 0.102 | 0.023 | 0.020 | 0.074 | 0.055 | 0.046 |

TABLE 3

| | AREA UNDER PLASMA CONCENTRATION-TIME CURVE (μg · h/mL) | |
|---|---|---|
| | COMPOUND (I) | EXAMPLE 1 |
| Dog 1 | 2.66 | 3.83 |
| Dog 2 | 0.77 | 4.16 |
| Dog 3 | 1.43 | 3.49 |
| Dog 4 | 2.68 | 4.54 |
| MEAN | 1.88 | 4.00 |
| STANDARD DEVIATION | 0.95 | 0.45 |

The invention claimed is:

1. A salt of (S)-7-(2-methoxy-3,5-dimethylpyridin-4-yl)-1-(tetrahydrofuran-3-yl)-1H-pyrazolo[4,3-c]quinolin-4(5H)-one formed with an acid selected from the group consisting of hydrochloric acid, hydrobromic acid, sulfuric acid, nitric acid, phosphoric acid, malonic acid, maleic acid, tartaric acid, methanesulfonic acid, benzenesulfonic acid and toluenesulfonic acid.

2. (S)-7-(2-methoxy-3,5-dimethylpyridin-4-yl)-1-(tetrahydrofuran-3-yl)-1H-pyrazolo [4,3-c]quinolin-4(5H)-one monomaleate salt according to claim 1.

3. (S)-7-(2-methoxy-3,5-dimethylpyridin-4-yl)-1-(tetrahydrofuran-3-yl)-1H-pyrazolo [4,3-c]quinolin-4(5H)-one monobenzenesulfonate salt according to claim 1.

4. A crystal of the salt according to claim 1.

5. A crystal of (S)-7-(2-methoxy-3,5-dimethylpyridin-4-yl)-1-(tetrahydrofuran-3-yl)-1H-pyrazolo [4,3-c]quinolin-4(5H)-one monomaleate salt according to claim 4, having a diffraction peak at a diffraction angle 2θ±0.2° of 10.1° in powder X-ray diffraction.

6. A crystal of (S)-7-(2-methoxy-3,5-dimethylpyridin-4-yl)-1-(tetrahydrofuran-3-yl)-1H-pyrazolo[4,3-c]quinolin-4(5H)-one monobenzenesulfonate salt according to claim 4, having a diffraction peak at a diffraction angle 2θ±0.2° of 9.9° in powder X-ray diffraction.

7. A pharmaceutical composition comprising the salt according to claim 1 as an active ingredient.

8. The crystal of (S)-7-(2-methoxy-3,5-dimethylpyridin-4-yl)-1-(tetrahydrofuran-3-yl)-1H-pyrazolo[4,3-c]quinolin-4(5H)-one monomaleate salt according to claim 5, having diffraction peaks at diffraction angles 2θ±0.2° of 9.1°, 10.1° and 11.1° in powder X-ray diffraction.

9. The crystal of (S)-7-(2-methoxy-3,5-dimethylpyridin-4-yl)-1-(tetrahydrofuran-3-yl)-1H-pyrazolo[4,3-c]quinolin-4(5H)-one monomaleate salt according to claim 5, having peaks at chemical shifts, ±0.5 ppm of 13.3, 61.9, 114.3, 138.9 and 172.0 in a $^{13}$C solid-state NMR spectrum.

10. The crystal of (S)-7-(2-methoxy-3,5-dimethylpyridin-4-yl)-1-(tetrahydrofuran-3-yl)-1H-pyrazolo [4,3-c]quinolin-4(5H)-one monobenzenesulfonate salt according to claim 6, having diffraction peaks at diffraction angles 2θ±0.2° of 9.9°, 13.7° and 14.6° in powder X-ray diffraction.

11. The crystal of (S)-7-(2-methoxy-3,5-dimethylpyridin-4-yl)-1-(tetrahydrofuran-3-yl)-1H-pyrazolo[4,3-c]quinolin-4(5H)-one monobenzenesulfonate salt according to claim 6, having peaks at chemical shifts, ±0.5 ppm of 16.8, 67.9, 114.0, 137.7 and 160.7 in a $^{13}$C solid-state NMR spectrum.

* * * * *